United States Patent
Just et al.

(10) Patent No.: US 11,839,423 B2
(45) Date of Patent: Dec. 12, 2023

(54) ABLATION CATHETER DESIGNS AND METHODS WITH ENHANCED DIAGNOSTIC CAPABILITIES

(71) Applicant: St. Jude Medical, Cardiology Division, Inc., St. Paul, MN (US)

(72) Inventors: Dale E. Just, Minneapolis, MN (US); D. Curtis Deno, Andover, MN (US); Ram K. Balachandran, Maple Grove, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 560 days.

(21) Appl. No.: 14/911,474

(22) PCT Filed: Oct. 28, 2014

(86) PCT No.: PCT/US2014/062562
§ 371 (c)(1),
(2) Date: Feb. 11, 2016

(87) PCT Pub. No.: WO2015/065966
PCT Pub. Date: May 7, 2015

(65) Prior Publication Data
US 2016/0192982 A1     Jul. 7, 2016

Related U.S. Application Data

(60) Provisional application No. 61/896,304, filed on Oct. 28, 2013.

(51) Int. Cl.
*A61B 18/14*     (2006.01)
*A61B 18/00*     (2006.01)
*A61B 17/00*     (2006.01)

(52) U.S. Cl.
CPC ............. *A61B 18/1492* (2013.01); *A61B 2017/00318* (2013.01); *A61B 2018/00077* (2013.01);
(Continued)

(58) Field of Classification Search
CPC . A61B 18/1492; A61B 18/1477; A61B 18/14; A61B 2017/00318;
(Continued)

(56) References Cited

U.S. PATENT DOCUMENTS

| 5,688,267 A | 11/1997 | Panescu et al. |
| 5,810,804 A | 9/1998 | Gough et al. |

(Continued)

FOREIGN PATENT DOCUMENTS

| CN | 101405052 A | 4/2009 |
| CN | 202776541 | 3/2013 |

(Continued)

OTHER PUBLICATIONS

Densford, Fink, "ACT Touts 1st-In-Human Trial for RF Ablation Tech", ACT Touts 1st-in-Human Trial for RF Ablation Tech, Jan. 26, 2016.

(Continued)

*Primary Examiner* — Linda C Dvorak
*Assistant Examiner* — Christine A Dedoulis
(74) *Attorney, Agent, or Firm* — Armstrong Teasdale LLP

(57) ABSTRACT

Electrode assemblies include segmented electrodes disposed on a catheter. The segmented electrodes can be constructed at the tip of the catheter or more proximally located. Tip electrodes can be constructed from an electrically-insulative substrate covered with a conductive material. The conductive material can be deposited on the electrically-insulative substrate to form a single tip electrode or multiple segmented electrodes. In some embodiments the tip electrode can include irrigation flow holes for irrigation. A method of (Continued)

manufacturing a tip electrode comprising a thin layer of conductive material deposited on an electrically-insulative substrate is disclosed. Segmented ring electrodes can be constructed from segmented ring electrodes that can be equally separated around a circumference of a catheter. The segmented ring electrodes can be formed into segmented electrode subassemblies that can then be joined to a catheter shaft.

11 Claims, 17 Drawing Sheets

(52) U.S. Cl.
CPC ........... *A61B 2018/00083* (2013.01); *A61B 2018/00107* (2013.01); *A61B 2018/00148* (2013.01); *A61B 2018/00577* (2013.01); *A61B 2018/00797* (2013.01); *A61B 2018/1405* (2013.01); *A61B 2218/002* (2013.01)

(58) Field of Classification Search
CPC .......... A61B 2018/00077; A61B 2018/00083; A61B 2018/00107; A61B 2018/00148; A61B 2018/00577; A61B 2018/00797; A61B 2018/1405; A61B 2018/00005; A61B 2018/00011; A61B 2018/00351; A61B 2018/1497; A61B 2218/002; A61B 2018/00815; A61B 2018/00821; A61B 2018/00791
See application file for complete search history.

(56) References Cited

U.S. PATENT DOCUMENTS

| | | | |
|---|---|---|---|
| 5,893,885 A * | 4/1999 | Webster, Jr. | A61B 18/1492 606/31 |
| 6,068,641 A | 5/2000 | Varsseveld et al. | |
| 6,113,591 A | 9/2000 | Whayne et al. | |
| 6,162,184 A | 12/2000 | Swanson et al. | |
| 6,171,275 B1 | 1/2001 | Webster, Jr. | |
| 6,197,021 B1 | 3/2001 | Panescu et al. | |
| 6,208,881 B1 | 3/2001 | Champeau | |
| 6,233,476 B1 | 5/2001 | Strommer et al. | |
| 6,241,724 B1 * | 6/2001 | Fleischman | A61B 18/1492 600/374 |
| 6,245,061 B1 | 6/2001 | Panescu et al. | |
| 6,405,067 B1 | 6/2002 | Mest et al. | |
| 6,477,396 B1 | 11/2002 | Mest et al. | |
| 6,498,944 B1 | 12/2002 | Ben-Haim et al. | |
| 6,500,172 B1 | 12/2002 | Panescu et al. | |
| 6,592,580 B1 | 7/2003 | Stockert | |
| 6,611,699 B2 * | 8/2003 | Messing | A61B 18/1492 600/372 |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 7,766,907 B2 | 8/2010 | Dando et al. | |
| 8,226,641 B2 * | 7/2012 | Potter | A61B 18/1492 606/41 |
| 8,414,579 B2 | 4/2013 | Kim et al. | |
| 2002/0022834 A1 | 2/2002 | Simpson et al. | |
| 2003/0004506 A1 | 1/2003 | Messing | |
| 2005/0070894 A1 * | 3/2005 | McClurken | A61B 18/1492 606/48 |
| 2008/0045943 A1 * | 2/2008 | Wittkampf | A61B 18/1492 606/41 |
| 2008/0097429 A1 | 4/2008 | McClurken et al. | |
| 2008/0114230 A1 | 5/2008 | Addis | |
| 2008/0161797 A1 | 7/2008 | Wang et al. | |
| 2009/0306653 A1 | 12/2009 | Anderson | |
| 2010/0168728 A1 | 7/2010 | Wang et al. | |
| 2011/0022046 A1 | 1/2011 | Wittkampf et al. | |
| 2011/0130817 A1 | 6/2011 | Chen | |
| 2011/0224667 A1 * | 9/2011 | Koblish | A61B 18/1492 606/41 |
| 2011/0313500 A1 | 12/2011 | Barker et al. | |
| 2012/0165812 A1 * | 6/2012 | Christian | A61B 18/1492 606/41 |
| 2012/0245576 A1 | 9/2012 | Epstein et al. | |
| 2013/0018434 A1 | 1/2013 | Zdeblick et al. | |
| 2013/0237977 A1 | 9/2013 | McCarthy et al. | |
| 2013/0338664 A1 | 12/2013 | Wang et al. | |
| 2014/0171821 A1 | 6/2014 | Govari et al. | |
| 2014/0276052 A1 | 9/2014 | Rankin et al. | |
| 2015/0273184 A1 * | 10/2015 | Scott | A61M 25/0045 29/842 |

FOREIGN PATENT DOCUMENTS

| | | |
|---|---|---|
| CN | 103237515 A | 8/2013 |
| EP | 1008327 A2 | 6/2000 |
| EP | 2842604 | 3/2015 |
| JP | 2009537243 A | 10/2009 |
| JP | 2010505596 A | 10/2010 |
| WO | 199819611 A1 | 5/1998 |
| WO | 200164283 A1 | 9/2001 |
| WO | 2005048858 A1 | 6/2005 |
| WO | 2012/091793 | 7/2012 |
| WO | 2014031800 | 2/2014 |
| WO | 2015065966 A1 | 7/2015 |
| WO | 2015130824 A1 | 9/2015 |

OTHER PUBLICATIONS

Rozen, Guy et al., PO02-153/PO02-153—Real Time Radiofrequency Ablation Lesion Assessment with a Novel Technology Using Contact Force Sensing and Elaborate Cather-Tissue Interface Temperature Measurement, HRS Presentation, May 14, 2015.

International search report and written opinion from European Patent Office in corresponding International Application No. PCT/US2016/025432, dated Aug. 24, 2016.

* cited by examiner

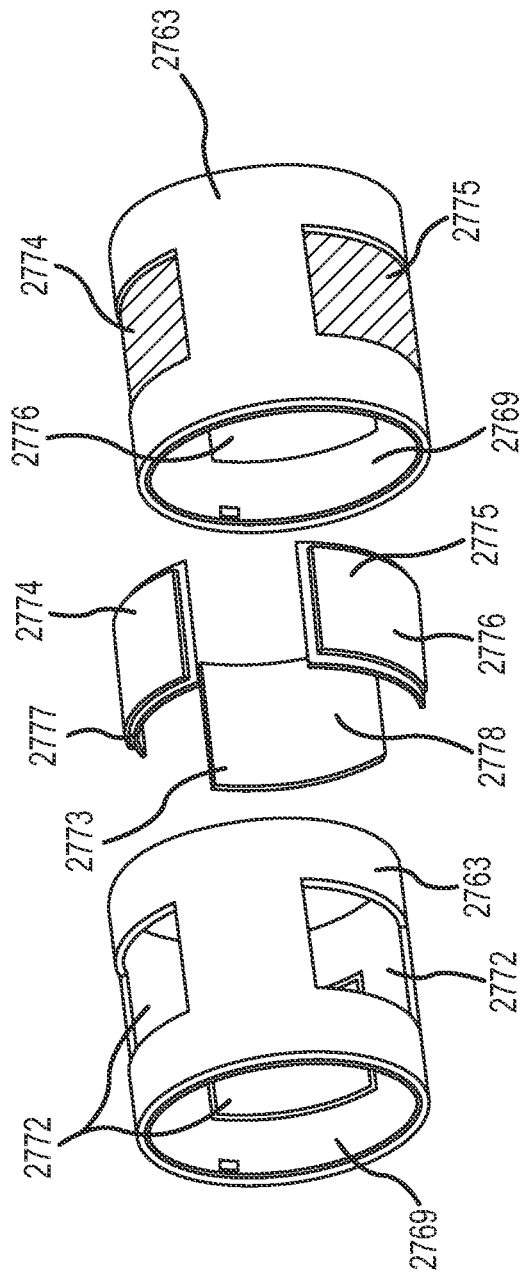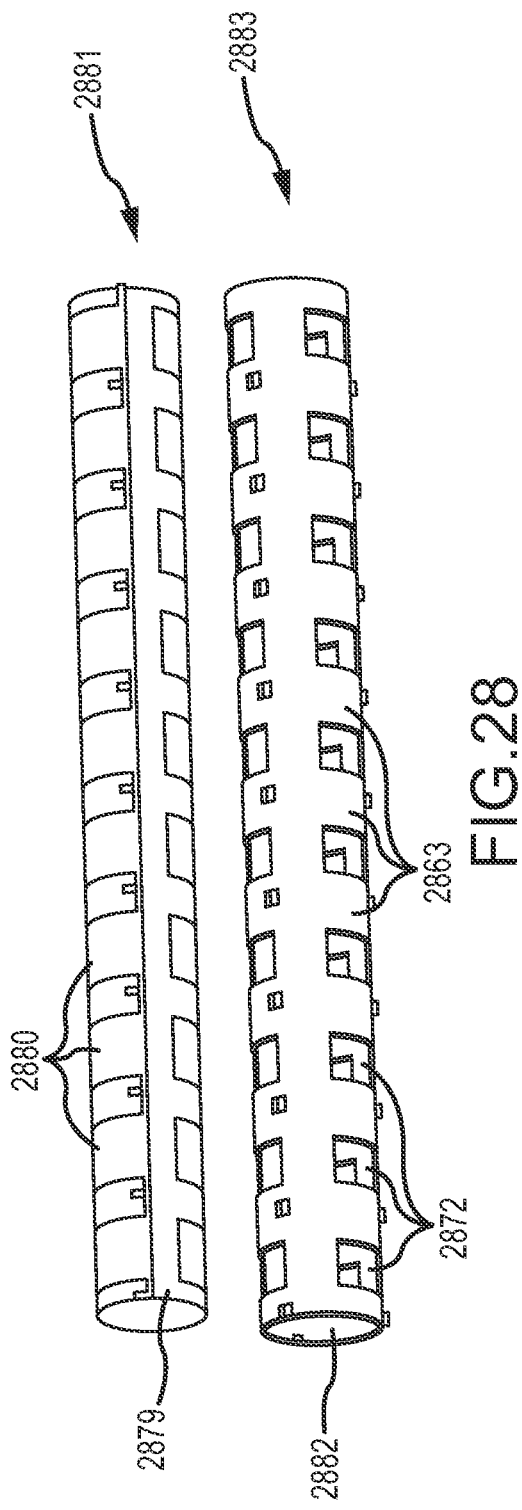

ABLATION CATHETER DESIGNS AND METHODS WITH ENHANCED DIAGNOSTIC CAPABILITIES

CROSS-REFERENCE TO RELATED APPLICATIONS

This application claims the benefit of U.S. provisional application No. 61/896,304, filed 28 Oct. 2013, which is hereby incorporated by reference as though fully set forth herein.

BACKGROUND a. Field

The instant disclosure relates generally to ablation catheter electrode assemblies. In particular, the instant disclosure relates to ablation catheter electrode assemblies comprising segmented electrodes. The instant disclosure further relates to methods of manufacturing ablation catheter electrode assemblies comprising segmented electrodes.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, or microwave ablation. An electrophysiology catheter imparts ablative energy to cardiac tissue to create one or more lesions in the cardiac tissue and oftentimes, a contiguous, and transmural lesion. This lesion disrupts undesirable cardiac activation pathways and thereby limits, corrals, or prevents errant conduction signals that can form or sustain arrhythmias.

It can be desirable to monitor and/or control the temperature of ablation electrode assemblies. It can also be desirable to use ablation electrode assemblies to provide irrigation fluid during RF ablation. RF ablation catheters can be configured to provide temperature feedback during RF ablation via a thermal sensor such as a thermocouple or thermistor. Typically, the temperature reading provided by a single thermal sensor cannot accurately represent the temperature of the electrode/tissue interface. One reason is because a portion of the electrode that is in direct contact with the targeted tissue can have a higher temperature than the rest of the electrode that is being cooled by the blood flow. The orientation of the RF ablation catheter can affect the position of the thermal sensor, and accordingly, can affect the temperature reading provided by the thermal sensor. If the thermal sensor is in contact with the targeted tissue, the thermal sensor can provide a certain temperature reading generally corresponding to the temperature of the targeted tissue. If the thermal sensor is not in contact with the targeted tissue due to the cooling effect of the blood flow, the thermal sensor can never approach the actual temperature of the targeted tissue. In an effort to overcome the effect that the orientation of the catheter can have on temperature sensing, multiple thermal sensors positioned at different locations on the electrode can be used. For example and without limitation, the highest measured temperature can be used to represent the electrode/tissue interface temperature.

The ability to assess lesion formation during ablation is a desirable feature. This is achieved in today's practice by monitoring electrograms (EGM's) from electrodes before, during and after RF ablation. Closely spaced electrodes, either at or near the ablation tip can potentially provide highly local information that can be used to assess the effectiveness of the ablation therapy. The additional sensing electrodes can also be used to characterize the electrophysiology of the local substrate. This can help to diagnose the arrhythmia and determine the site for ablation.

BRIEF SUMMARY

The instant disclosure, in at least one embodiment, relates to a tip electrode of a catheter comprising an electrically-insulative substrate comprising a receiving lumen, a plurality of irrigation flow holes, a tip portion, and a proximal portion. A thin layer of conductive material can be deposited on an outer surface of the tip portion. An inner surface of the electrically-insulative substrate can define the receiving lumen, and irrigation flow holes can extend radially through the electrically-insulative substrate and terminate adjacent an outer surface of the electrically-insulative substrate. The receiving lumen can be fluidly coupled to the plurality of irrigation flow holes and the receiving lumen is configured to be fluidly coupled to a catheter body. The fluid coupling of the irrigation flow holes to the receiving lumen and the receiving lumen to a catheter body can allow for an irrigant to be supplied from a proximal end of the catheter and distributed around an outer surface of the tip electrode. In one embodiment a thermal sensor channel can be located on the outer surface of the electrically-insulative substrate. In other embodiments a through channel can extend from the inner surface to an outer surface of the electrically-insulative substrate. A thermal sensor can be set within the through channel and thermally coupled to the thin layer of conductive material. The tip electrode can further comprise a fluid lumen alignment feature coupled to the inner surface of the electrically-insulative substrate and configured for coupling with an irrigation sleeve, and an electrical conductor termination recess at the distal end of the tip electrode and configured for coupling to a conductor wire. In one embodiment the tip electrode can further comprise an insulation sleeve configured to circumferentially surround and electrically insulate the proximal portion of the tip electrode. In other embodiments the tip electrode can further comprise a deflection pull ring comprising at least one clip lock configured to mate with a relief opening of the insulation sleeve.

In an embodiment of the disclosure, a segmented tip electrode can comprise an electrically-insulative substrate comprising a receiving lumen, a plurality of irrigation flow holes, a tip portion, and a proximal portion. A plurality of equally spaced longitudinally extending segmented electrodes comprising a thin layer of conductive material can be deposited on an outer surface of the tip portion. An inner surface of the electrically-insulative substrate can define the receiving lumen and irrigation flow holes can extend radially through the electrically-insulative substrate and terminate adjacent an outer surface of the electrically-insulative substrate. The receiving lumen can be fluidly coupled to the plurality of irrigation flow holes and the receiving lumen is configured to be fluidly coupled to a catheter body. The fluid coupling of the irrigation flow holes to the receiving lumen and the receiving lumen to a catheter body can allow for an irrigant to be supplied from a proximal end of the catheter and distributed around an outer surface of the tip electrode. In one embodiment a thermal sensor channel can be located on the outer surface of the electrically-insulative substrate. In other embodiments a through channel can extend from the inner surface to an outer surface of the electrically-insulative substrate. A thermal sensor can be set within the through channel and thermally coupled to the thin layer of conductive material. The tip electrode can further comprise a fluid lumen alignment feature coupled to the inner surface of the electrically-insulative substrate and configured for coupling with an irrigation sleeve, and an electrical conductor termination recess at the distal end of the tip electrode and configured for coupling to a conductor wire. In one embodiment the tip electrode can further comprise an insulation sleeve configured to circumferentially surround and electrically insulate the proximal portion of the tip electrode. In other embodiments the tip electrode can further comprise a deflection pull ring comprising at least one clip lock configured to mate with a relief opening of the insulation sleeve. The plurality of equally spaced longitudinally extending segmented electrodes can comprise four equally spaced longitudinally extending segmented electrodes. In one embodiment the plurality of irrigation flow holes are formed between the plurality of equally spaced longitudinally extending segmented electrodes.

In one embodiment of the disclosure a segmented ring electrode is provided. The segmented ring electrode comprises an inner electrode support, a layer of deposited conductive material, an outer support segment, a polymeric skin, a plurality of electrode segments; and a plurality of conductor wires. The outer support segment can comprise a plurality of notches. The conductive material can be deposited on an outer surface of the inner electrode support to form a plurality of receivers. The plurality of electrode segments can each be electrically coupled to a separate receiver, and the outer support segment can be configured to circumferentially surround the inner electrode support. The plurality of notches of the outer support segment can be configured to overlay an electrode ridge on each of the plurality of electrode segments. The plurality of conductor wires can each be configured to electrically couple to a separate receiver.

BRIEF DESCRIPTION OF THE DRAWINGS

FIG. 27 depicts isometric views of components of a segmented electrode subassembly.

FIG. 28 depicts isometric views of one method of manufacturing segmented electrode subassemblies in accordance with an embodiment of the disclosure.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
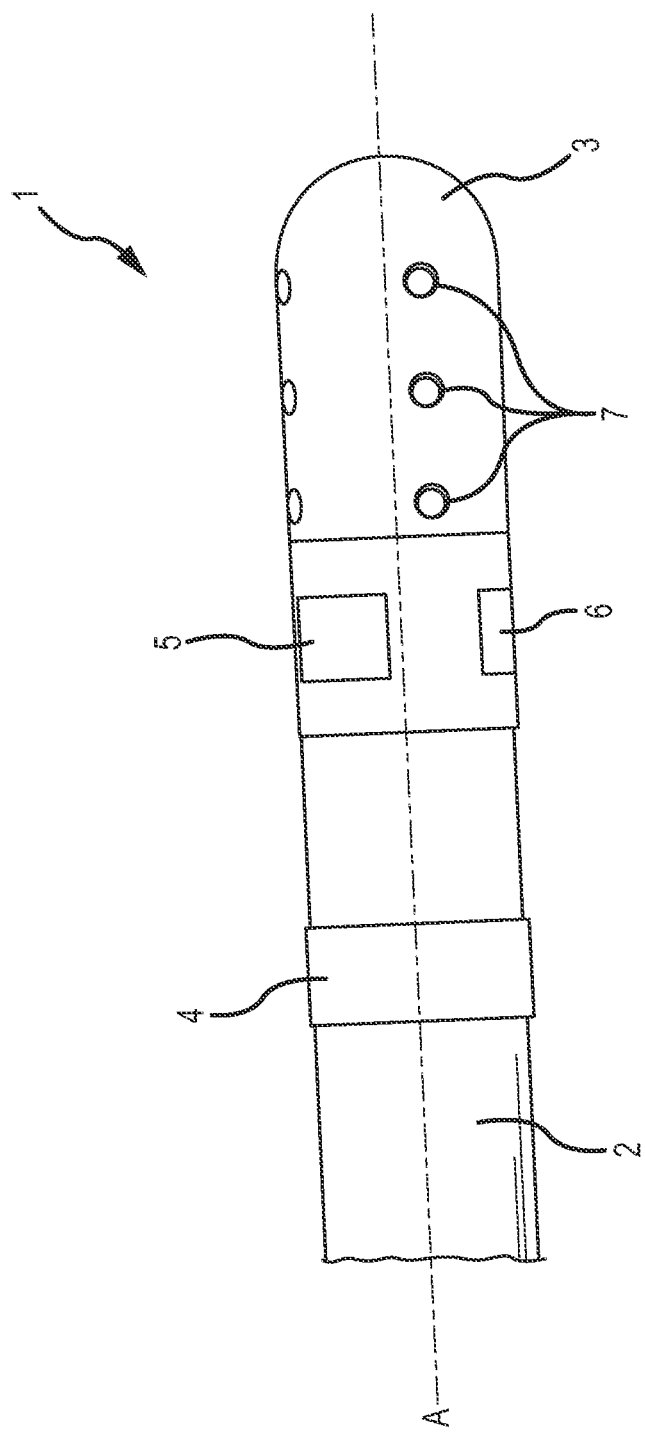
FIG. 1 is a fragmentary, diagrammatic view of one embodiment of a distal portion of a segmented electrode catheter.

An embodiment of a catheter assembly 1 is generally shown in FIG. 1. The catheter assembly 1 can comprise a ring electrode 4, a plurality of segmented ring electrodes 5, 6, and a tip electrode 3. The catheter assembly 1 can comprise part of an irrigated or non-irrigated catheter system for examination, diagnosis, and/or treatment of internal body tissues (e.g. targeted tissue areas). In an exemplary embodiment, the catheter assembly 1 can comprise an ablation catheter (e.g. radio frequency (RF), cryoablation, ultrasound, etc.). The instant disclosure refers to RF ablation electrodes and electrode assemblies, but it is contemplated that the instant disclosure is equally applicable to any number of other ablation electrodes and electrode assemblies.

Catheter assembly 1 can comprise a ring electrode 4 coupled to a catheter shaft 2, at least one segmented ring electrode coupled to the catheter shaft 2, and a tip electrode 3 coupled to a distal end of the catheter shaft 2. In the current embodiment the ring electrode 4 is disposed proximal to other electrodes that are present on the shaft. However in other embodiments, a ring electrode 4 can be provided more distal on the shaft or can be a first ring electrode 4 among several ring electrodes present on the catheter shaft 2. At least one segmented ring electrode can comprise a single segmented electrode coupled to the catheter shaft 2. In an exemplary embodiment a first segmented ring electrode 5, a second segmented ring electrode 6, and a third segmented ring electrode (not shown) are disposed equidistantly on a circumference around a longitudinal axis A of the catheter shaft 2. In other embodiments, at least one segmented electrode can be coupled to the catheter shaft 2 in various configurations to suit specific purposes desired by a user of the catheter assembly 1. The tip electrode 3 can comprise a plurality of irrigation flow holes 7.

The tip electrode 3 can comprise a thin layer of conductive material clad or deposited onto an electrically-insulative substrate. The electrically-insulative substrate can either be made of ceramic materials or polymers of various durometers. The electrically-insulative substrate can be an injection molded component. The electrically-insulative substrate can be formed in various configurations according to the desired use of the catheter. These configurations can include irrigation lumens, irrigation flow holes, sensor channels, and/or conductive channels as well as structures for mechanical attachment, alignment, or stabilization. The conductive material can be selectively bonded to, deposited, or coated onto the electrically-insulative substrate by various techniques, including low temperature print manufacturing (with or without sintering), electroplating, electroless plating, sputter deposition, heat, mechanical deformation, cathodic arc deposition, evaporative deposition and pulsed laser deposition or combinations thereof.

The thin layer of conductive material deposited onto the electrically-insulative substrate can improve temperature correlation between the electrode and tissue interface because it is configured as a thin layer of heat and electrically conducting material, in place of a solid mass. The thin layer can also mitigate temperature gradients across the tip electrode 3. The thin layer of conductive material can be electrically connected to an ablation system to allow for the delivery of ablative energy or the like. The thin layer of conductive material can be electrically connected to the ablation system in any manner conventional in the art. For example, a power wire can be provided. The power wire can extend through a lumen within the catheter shaft 2.

The ring electrode 4 and at least one segmented ring electrode 5, 6 can be used, for example, with a visualization, navigation, and mapping system. The ring electrode 4 and at least one of the segmented ring electrodes can be configured to provide a signal indicative of both the position and orientation of at least a portion of the catheter shaft 2. The visualization, navigation, and/or mapping system with which the ring electrode 4 and the at least one segmented electrode can be used can comprise an electric field-based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the electrodes can be configured to be responsive to an electric field transmitted within the body of the patient. The electrodes can be used to sense impedance at a particular location and transmit a representative signal to an external computer or processor.

In other exemplary embodiments, however, the visualization, navigation, and/or mapping system can comprise other types of systems, such as, for example and without limitation: a magnetic field-based system such as the CARTO System (now in a hybrid form with impedance- and magnetically-driven electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the catheter shaft can comprise metallic coils that can be configured to be responsive to a magnetic field transmitted through the body of the patient. The magnetic coils can be used to sense the strength of the field at a particular location and transmit a representative signal to an external computer or processor. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the catheter shaft can comprise both one or more impedance-based electrodes and one or more magnetic coils. Commonly available fluoroscopic, computed tomography (CT), and magnetic resonance imaging (MRI)-based systems can also be used.

The catheter assembly 1 can further comprise additional lumens for receiving other components. The catheter assembly 1 can also further comprise a cable connector or interface (not shown) and a handle (not shown). The cable connector or interface can provide mechanical, fluid, and electrical connections for cables extending from the handle. The cable connector or interface can be conventional in the art and can be disposed at the proximal end of the handle. The handle can provide a location for the clinician to hold the catheter assembly 1 and can further provide means for steering or guiding the catheter shaft 2 within a body as known in the art. Catheter handles are generally conventional within the art and it will be understood that the construction of the handle can vary. In an embodiment, for the purpose of steering the catheter shaft 2 within a body, the handle can be substituted by a controllable robotic actuator.

Figure 2:
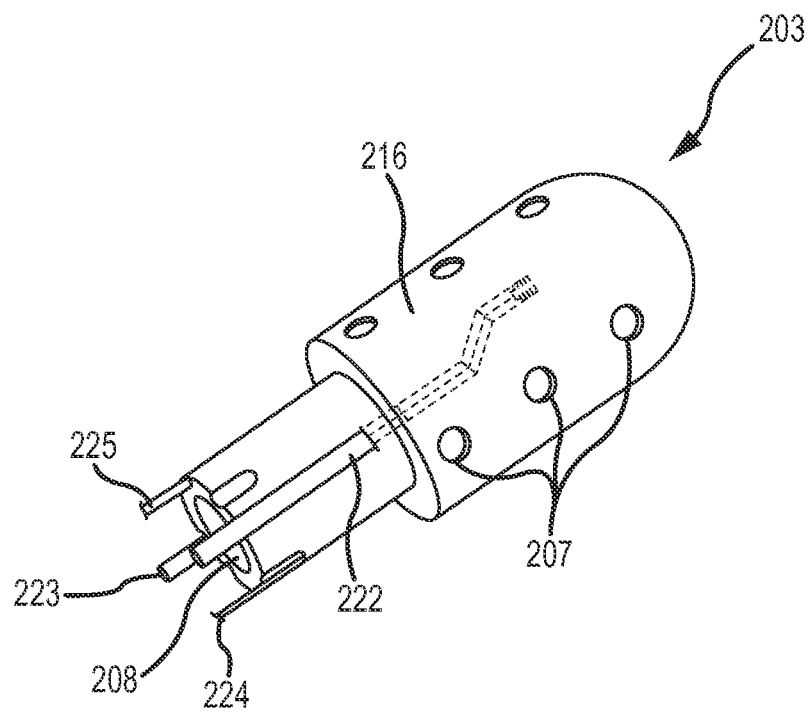
FIG. 2 is an isometric view of an embodiment of a tip electrode with a thin outer layer of conductive material.

FIG. 2 illustrates an embodiment of a tip electrode 203 comprising a plurality of irrigation flow holes 207, a receiving lumen 208, a first thermocouple 222, a second thermocouple 223, a third thermocouple 224, and a fourth thermocouple 225. In this embodiment, the thermocouples are disposed beneath the outer surface of the tip electrode 203 and spaced equidistantly around the circumference of its outer surface. The receiving lumen 208 can be configured to accept an irrigation lumen (not shown) or to otherwise couple to a fluid delivery device that can supply irrigation through the irrigation flow holes 207. The irrigation lumen can be connected to a fluid source providing a biocompatible fluid such as saline, or a medicament, through a pump, which can comprise, for example, a fixed rate roller pump or variable volume syringe pump with a gravity feed supply from the fluid source for irrigation. The fluid source and/or pump is conventional in the art. The fluid source and/or pump can comprise a commercially available unit sold under the name Cool Point™, available from St. Jude Medical, Inc. in an embodiment.

Figure 3:
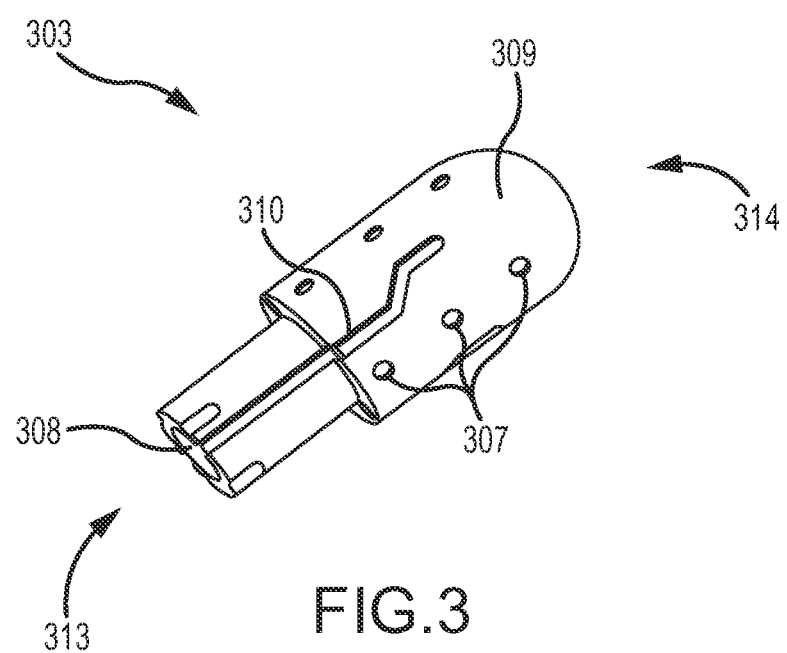
FIG. 3 depicts an isometric view of an embodiment of an unclad tip electrode.

The tip electrode 203 can comprise an electrically-insulative substrate (as shown in FIG. 3) with a thin layer of conductive material 216 deposited over the electrically-insulative substrate. The conductive material 216 can be bonded to or deposited on the electrically-insulative substrate of the tip electrode 203 in a variety of ways. The conductive material can be selectively bonded to, deposited, or coated onto the electrically-insulative substrate by various techniques, including low temperature print manufacturing (with or without sintering), electroplating, electroless plating, sputter deposition, heat, mechanical deformation, cathodic arc deposition, evaporative deposition and pulsed laser deposition. It is also contemplated that a combination of the above methods can be used to deposit the conductive material 216 on the electrically-insulative substrate.

The tip electrode 203 can be connected to and/or coupled with a catheter shaft. The lengths and/or diameter of the tip electrode 203 can vary depending on the design of the catheter. In one embodiment, the tip electrode 203 can be about 4 millimeters in length.

In some embodiments the electrically-insulative substrate can comprise a thermally insulative material. In such embodiments the electrically-insulative substrate can provide an insulated internal flow path for irrigation fluid. The electrically-insulative substrate can thermally isolate the multiple thermal sensors located within the tip electrode 203. By thermally isolating the temperature sensors, the tip electrode 203 can have an improved ability to measure the temperature at the tip-tissue interface during lesion formation.

FIG. 3 illustrates a partially assembled, unclad embodiment of a tip electrode 303. The unclad embodiment of the tip electrode 303 comprises an electrically-insulative substrate 309 that has been formed through one of the previously described methods. The illustrated embodiment can comprise at least one thermal sensor channel 310, a plurality of irrigation flow holes 307, and a receiving lumen 308. In a preferred embodiment the unclad tip electrode 303 comprises four separate thermal sensor channels that are equally distributed around an outer circumference of the tip electrode 303. The thermocouples can be placed within the thermal sensor channels. The separate thermal sensor channels can further be situated such that they are disposed between the irrigation flow holes 307.

In one embodiment of the disclosure, the electrically-insulative substrate 309 can comprise a thermal insulator having a reduced thermal conductivity. In this embodiment the electrically-insulative substrate 309 has lower thermal conductivity, and preferably substantially lower, than an electrically conductive cladding that can be applied to the substrate. The electrically-insulative substrate 309 can comprise polymer with low thermal conductivity in accordance with an embodiment of the disclosure. A polymer with low thermal conductivity can significantly reduce heat conduction from the tip onto the other structural components that comprise the tip. One example of a polymer with low thermal conductivity that can be used in conjunction with the instant disclosure is polyether ether ketone (PEEK). Additional examples of thermally nonconductive or materials with low thermal conductivity that can be useful in conjunction with the instant disclosure include, but are not limited to, high density polyethylene (HDPE), polyimide thermoplastic resins, such as ULTEM® as provided by General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. The electrically-insulative substrate 309 can also comprise other plastic materials such as silicone or polyether block amides such as those sold under the trademark PEBAX® and generally available from Arkema France in other embodiments of the disclosure.

The tip electrode 303 has a distal end 314 and a proximal end 313. In one embodiment of the disclosure, the tip electrode 303 can be generally cylindrical in shape and the distal end 314 of the tip electrode 303 can be partially spherical or generally hemispherical in shape. The proximal end 313 of the tip electrode 303 can be configured for coupling and/or connecting the tip electrode 303 to a catheter shaft. The proximal end 313 of the tip electrode 303 can also be configured to receive an irrigation tube through the receiving lumen 308. The electrically-insulative substrate 309 of the tip electrode 303 can comprise multiple lumens for receiving any number of components (e.g. wires and the like) which can be routed through the electrically-insulative substrate 309.

Figure 4:
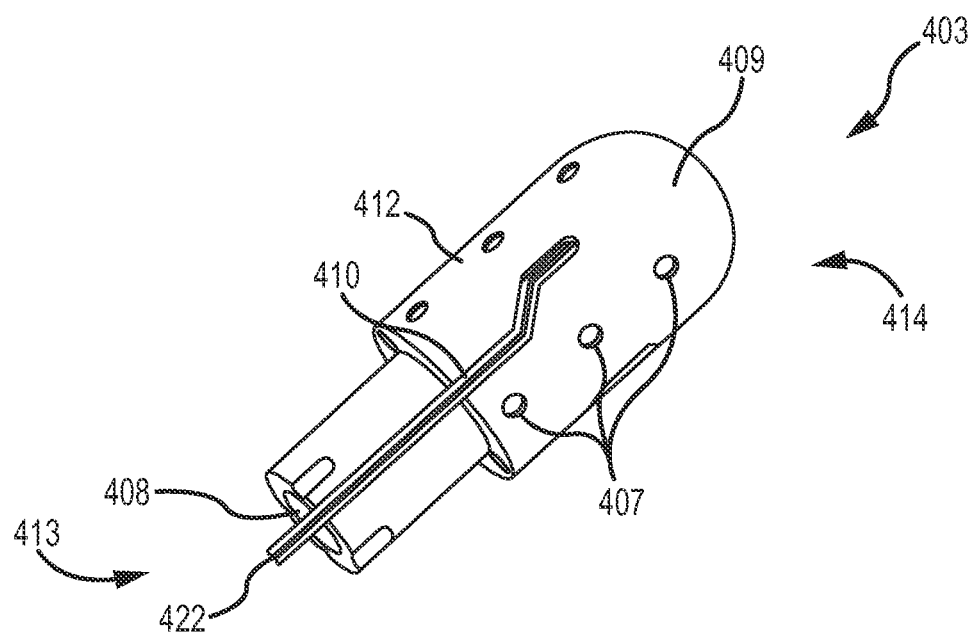
FIG. 4 is an isometric view of an embodiment of an unclad tip electrode including a thermal sensor.

FIG. 4 illustrates an unclad embodiment of a tip electrode 403 where a thermocouple 422 has been placed within a thermal sensor channel 410. The unclad tip electrode 403 also comprises a plurality of irrigation flow holes 407 and a receiving lumen 408. An outer surface 412 of the tip electrode 403 comprises a thermal sensor channel 410. In one embodiment the outer surface 412 of the tip electrode 403 can comprise a plurality of thermal sensor channels 410 where each of the thermal sensor channels 410 are configured to receive a thermocouple or other thermal sensor. The illustrated embodiment shows the thermocouple 422 in the thermal sensor channel 410. In accordance with one embodiment of the disclosure the tip electrode 403 can comprise four thermal sensor channels and can also comprise four thermal sensors. The thermal sensors can be equally spaced around the periphery or circumference of the electrically-insulative substrate 409. Although four thermal sensors that are equally spaced are mentioned in detail, the electrically-insulative substrate 409 can include fewer or more thermal sensors in other embodiments and the location of the thermal sensors can vary in other embodiments. The thermal sensors can be configured for temperature measurement and control and/or regulation of RF energy supplied to the tip electrode 403. In some embodiments, the thermal sensors comprise thermocouples and/or thermistors. The thermal sensors can also comprise other devices, such as for example and without limitation, devices for determining pressure, temperature, and a flow-related parameters of a flowing fluid.

Figure 5:
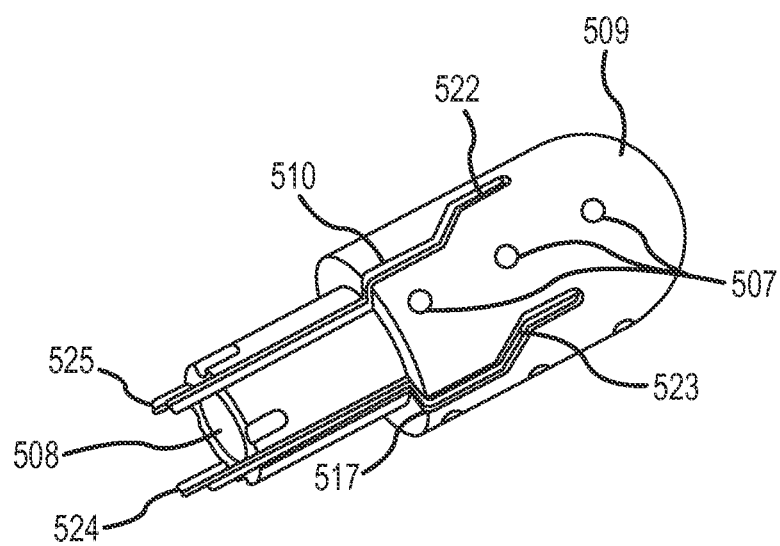
FIG. 5 is an isometric view of another embodiment of an unclad tip electrode with a plurality of thermal sensors.

FIG. 5 illustrates an unclad embodiment of a tip electrode 503 where a first thermocouple 522 has been placed in a first thermal sensor channel 510 and a second thermocouple 523 has been placed in a second thermal sensor channel 517. A third thermocouple 524 and a fourth thermocouple 525 are also shown and are disposed roughly 90 degrees apart around a circumference of the receiving lumen 508.

Figure 6:
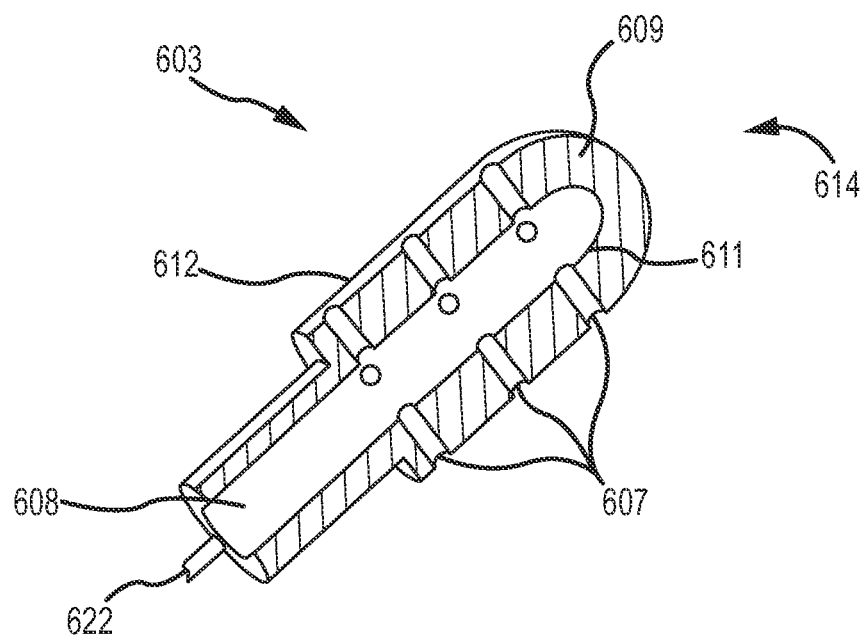
FIG. 6 is a cross-sectional view of an embodiment of an unclad tip electrode showing the through channels on the electrically-insulative substrate.

FIG. 6 illustrates a cross-sectional view of an unclad embodiment of a tip electrode 603. The tip electrode 603 can be formed of an electrically-insulative substrate 609 comprising a receiving lumen 608, a plurality of irrigation flow holes 607, and a first thermocouple 622. The plurality of irrigation flow holes 607 are coupled to the receiving lumen 608 as part of the flow path. The tip electrode 603 includes an inner surface 611 and an outer surface 612. The inner surface 611 of the tip electrode 603 defines the receiving lumen 608. The receiving lumen 608 includes an irrigation flow hole 607 that extends from the inner surface 611 to the outer surface 612 of the tip electrode 603. In one embodiment, the tip electrode 603 can comprise a plurality of irrigation flow holes 607. In one embodiment, the irrigation flow holes 607 can be oriented at about 90 degrees relative to a longitudinal axis of the tip electrode 603. In accordance with other embodiments, the irrigation flow holes 607 can be angled generally toward a distal end 614 of the tip electrode 603 at an acute angle (e.g., between about 20 to about 70 degrees, and for some embodiments, between about 30 to about 65 degrees) with respect to a longitudinal axis of the tip electrode 603. The orientation of the irrigation flow holes 607 can vary depending on the design of the tip electrode 603.

Figure 7:
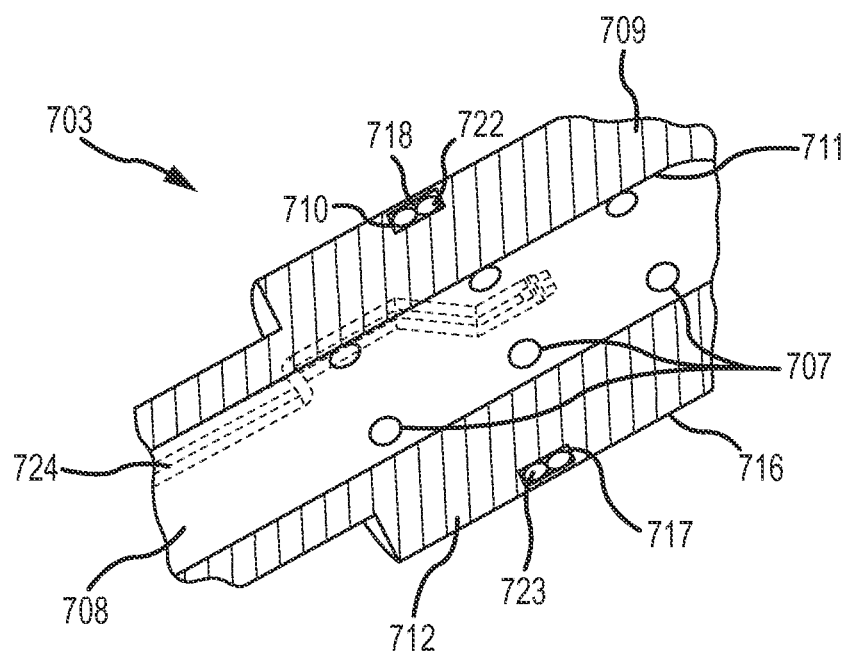
FIG. 7 depicts a cross-sectional view of an embodiment of an electrode including a plurality of thermal sensors set within the thermal sensor channels on the outer surface.

FIG. 7 illustrates a cross-section of another partially assembled, unclad embodiment of a tip electrode 703. The tip electrode 703 can comprise an electrically-insulative substrate 709, a receiving lumen 708, and a cladding 716. The electrically-insulative substrate 709 can be formed to comprise an inner surface 711, an outer surface 712, and at least one irrigation flow hole 707. The inner surface 711 of the electrically-insulative substrate 709 defines a receiving lumen 708. The receiving lumen 708 can be fluidly connected to the at least one irrigation flow hole 707 and configured to be fluidly connected to an irrigation lumen. The at least one irrigation flow hole 707 extends from the receiving lumen 708 through the electrically-insulative substrate 709 and the cladding 716. It then terminates adjacent to the outer surface 712. At least one irrigation flow hole 707 allows for irrigation to pass through an irrigation lumen in a catheter shaft, into the receiving lumen 708 within the tip electrode 703, and out through the irrigation flow hole 707 to a target tissue or ablation site adjacent to the tip electrode 703. In one embodiment, the electrically-insulative substrate 709 can comprise at least one thermal sensor channel. The illustrated embodiment of FIG. 7 shows a first thermal sensor channel 710 and a second thermal sensor channel 717. A thermal sensor can be operably coupled to each thermal sensor channel. In the displayed embodiment a first thermocouple 722 is disposed within the first thermal sensor channel 710 and a second thermocouple 723 is disposed within the second thermal sensor channel 717. An outline of a third thermocouple 724 that is shown, and can be placed within a separate thermal sensor channel (not shown). By placing the thermal sensors within a thermal sensor channel the thermal sensor can be set below an outer surface 712 of the electrically-insulative substrate 709. A filler material 718 can then be used to secure the thermal sensor in place within the thermal sensor channel. The filler material 718 can comprise a thermally conductive epoxy or other material. In one embodiment the filler material 718 can be thermally conductive. An increased thermal conductivity can allow for an increased rate of heat transfer to the filler material 718 and a faster response time by the thermal sensor to any changes in temperature of the tip electrode 703 in the area surrounding the thermal sensor. In one embodiment the insulative properties of the electrically-insulative substrate 709 impedes the effect any irrigation fluid flowing through the receiving lumen 708 and the irrigation flow holes 707 may have on temperature readings taken by the thermal sensors included in the tip electrode 703.

Figure 8:
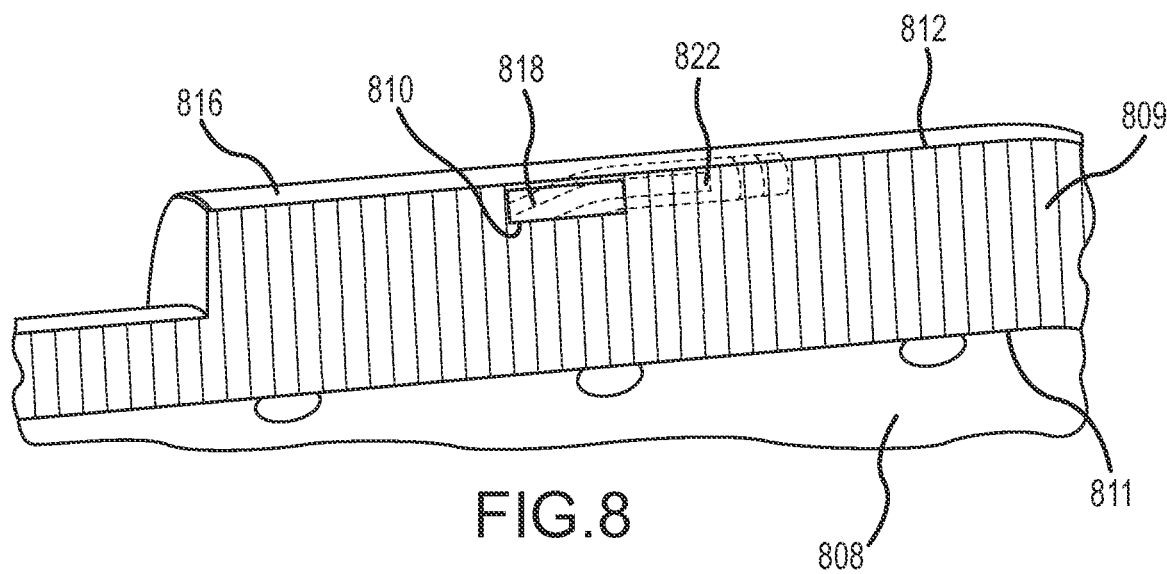
FIG. 8 depicts a close-up, cross-sectional view of a portion of a tip electrode showing the tip of the thermal sensor.

FIG. 8 illustrates the called out section of the embodiment of FIG. 7. The electrically-insulative substrate 809 comprises an inner surface 811, an outer surface 812, a receiving lumen 808, a plurality of irrigation flow holes 807, and a thermal sensor channel 810. The electrically-insulative substrate 809 is clad with a thin layer of conductive material 816. A thermocouple 822 is shown disposed along the electrically-insulative substrate 809 and set within the thermal sensor channel 810. The thermocouple 822 can be glued within the thermal sensor channel 810 and placed in thermal contact with the conductive material 816 by a filler material 818.

Figure 9:
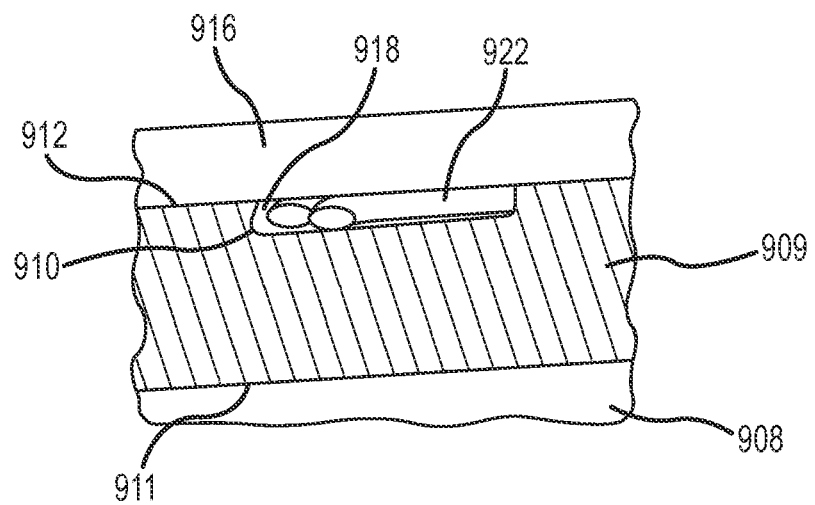
FIG. 9 depicts another close-up, cross-sectional view of a portion of a tip electrode showing the tip of the thermal sensor according to an embodiment of the disclosure.

FIG. 9 shows another embodiment of a tip electrode according to the disclosure. The electrically-insulative substrate 909 can comprise an inner surface 911, an outer surface 912, a receiving lumen 908, and a thermal sensor channel 910. The thermal sensor channel 910 can allow for a thermocouple 922 to be operably coupled thereto. The thermocouple 922 is disposed within the electrically-insulative substrate 909 and held in place with a filler material 918 such that it is thermally insulated from an irrigant flowing through the receiving lumen 908. The thermocouple 922 can also be thermally coupled to an electrically conductive material 916 that can be clad on an outer surface 912 of the electrically-insulative substrate 909.

Figure 10:
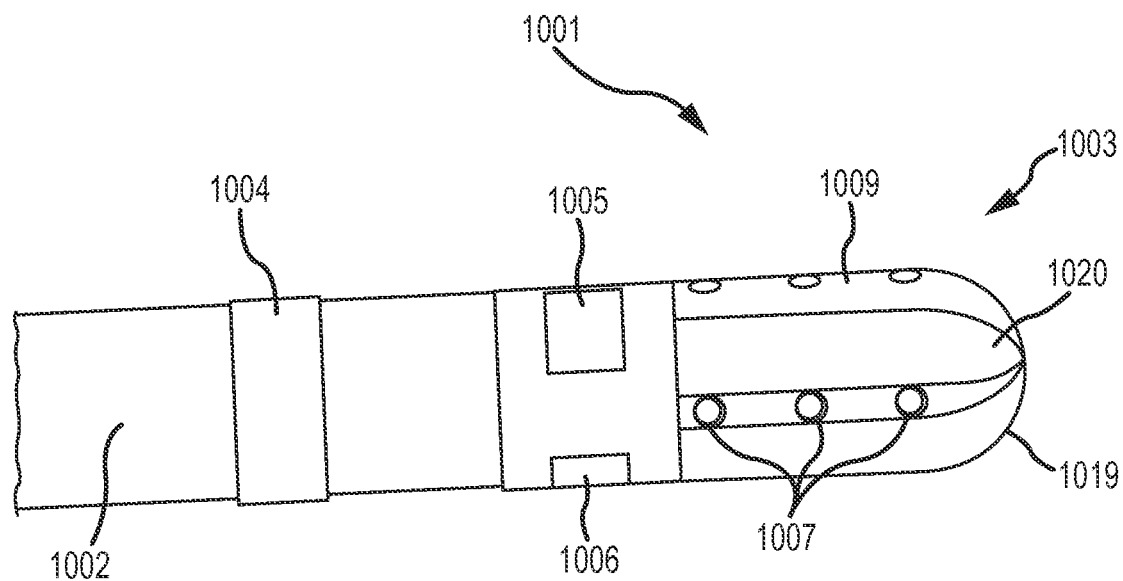
FIG. 10 is a diagrammatic view of the distal portion of one embodiment of a segmented tip and segmented ring electrode catheter.

FIG. 10 illustrates an embodiment of a catheter assembly 1001 comprising a catheter shaft 1002, a ring electrode 1004, a first segmented ring electrode 1005, a second segmented ring electrode 1006, and a tip electrode 1003. In the displayed embodiment, the tip electrode 1003 can further comprise a plurality of segmented tip electrodes and a plurality of irrigation flow holes 1007. A first segmented tip electrode 1019 and a second segmented tip electrode 1020 can be seen in FIG. 10. The tip electrode 1003 can further include third and fourth segmented tip electrodes (not shown). The plurality of segmented tip electrodes extend lengthwise along the tip electrode 1003 parallel to the length of the catheter. The plurality of segmented tip electrodes are electrically insulated from each other by an electrically-insulative substrate 1009. The electrically-insulative substrate 1009 can also comprise a plurality of irrigation flow holes therethrough. The plurality of irrigation flow holes 1007 can be configured to deliver an irrigation fluid to the exterior of the catheter assembly 1001. While the illustrated embodiment displays the ring electrode 1004 placed proximal to the first and second segmented ring electrodes 1005,1006, in other embodiments the ring electrode 1004 can be placed distal to the segmented ring electrodes or can also be comprised of several segmented electrodes.

Figure 11:
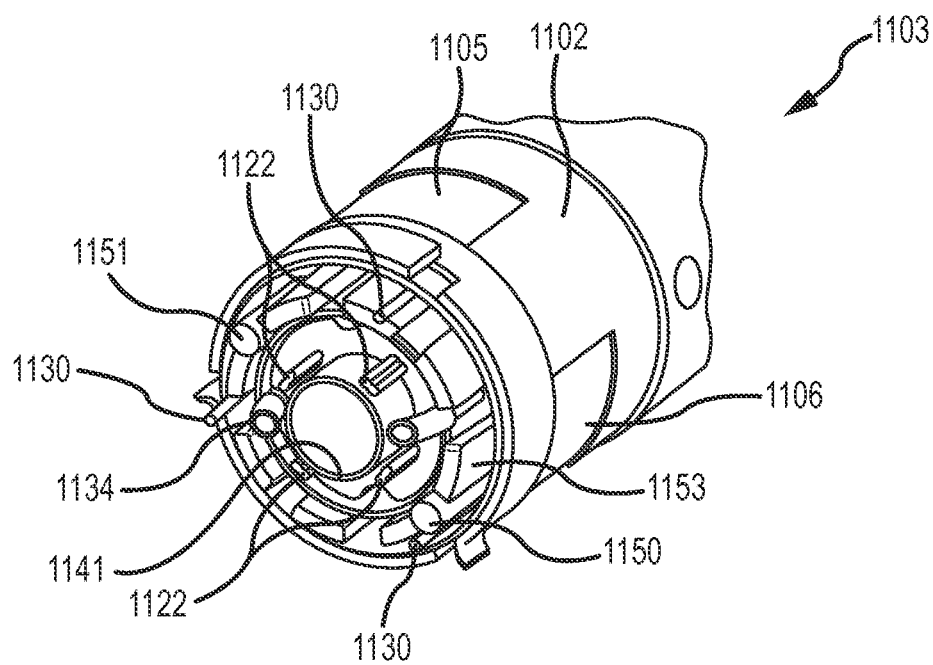
FIG. 11 is an isometric, fragmentary, cross-sectional view of an embodiment of a segmented tip electrode catheter.

FIG. 11 illustrates a cross-sectional view of an embodiment of the disclosure. A tip electrode 1103 is coupled to a distal end of a catheter shaft 1102. The catheter shaft 1102 can comprise a first segmented ring electrode 1105, a second segmented ring electrode 1106, and a third segmented ring electrode (not shown) that are operably coupled to the catheter shaft 1102 proximal of the tip electrode 1103. The catheter shaft 1102 can further comprise a deflection pull ring 1153, an irrigation sleeve 1141, at least one thermal sensor 1122, and at least one ablation electrode wire 1134. The first, second, and third segmented ring electrodes 1105, 1106, (not shown) can each be electrically coupled to a separate electrode conductor wire 1130. The tip electrode 1103 can be electrically coupled to at least one ablation electrode wire 1134 The deflection pull ring 1153 can be operably coupled to a first pullwire 1150 and a second pullwire 1151 which can operate to deflect the catheter shaft 1102

Figure 12:
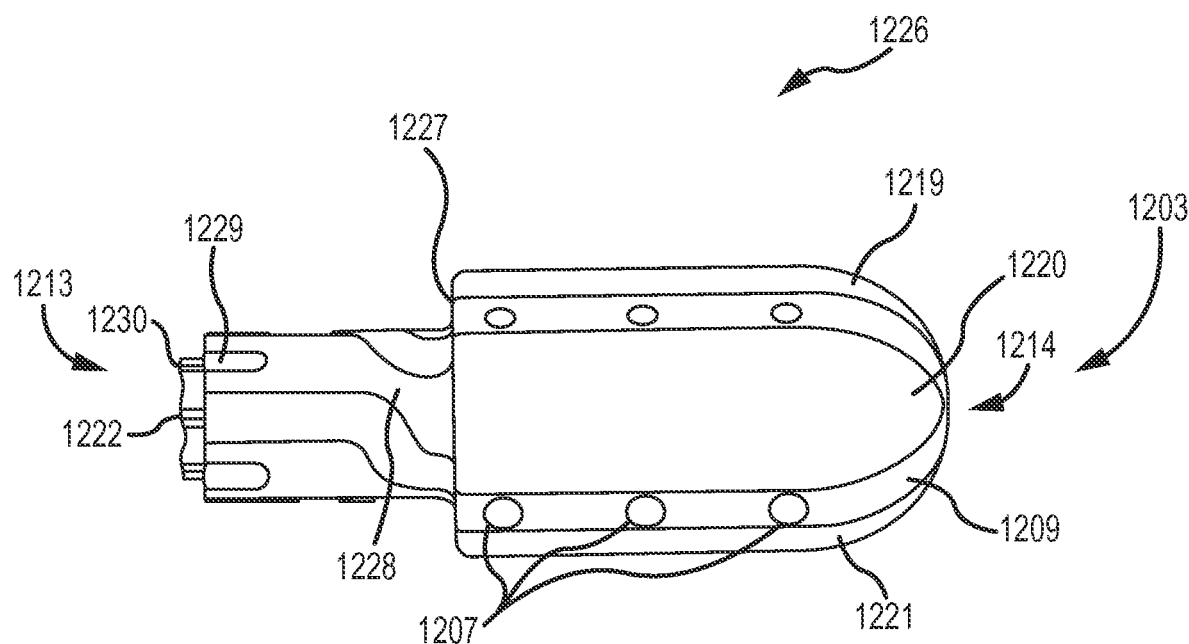
FIG. 12 depicts a diagrammatic view of a segmented tip ablation electrode assembly in accordance with an embodiment of the disclosure.

FIG. 12 shows another embodiment of a tip electrode 1203 comprising a plurality of segmented electrodes. The tip electrode 1203 comprises a plurality of segmented tip electrodes. The current embodiment can comprise a first segmented tip electrode 1219, a second segmented tip electrode 1220, a third segmented tip electrode 1221, and a fourth segmented tip electrode (not shown). Each of the plurality of segmented tip electrodes can be electrically and thermally separated from each other by an underlying strip of electrically-insulative substrate 1209. The segmented tip electrodes can comprises thin layers of conductive material deposited on a substrate. In some embodiments the substrate can be an electrically-insulative substrate. The thin layers of conductive material can be deposited onto the substrate through a variety of manufacturing methods. These can include low temperature print manufacturing, electroplating, sputter deposition, mechanical assembly and deformation and/or heating, and pulsed laser deposition or combinations of these methods. In the illustrated embodiment the tip electrode 1203 comprises four equally sized and equally spaced segmented tip electrodes extending along a longitudinal axis of the tip electrode 1203. The thin conductive material that comprises each of the segmented tip electrodes includes an electrical conductor termination recess 1229 at a proximal end 1213 of the tip electrode 1203. The thin conductive material can be placed on the tip electrode 1203 so that it shifts circumferentially on the tip electrode 1203 proximal of the shoulder 1227 (as seen in FIG. 12), and terminates adjacent a distal end 1214 of the tip electrode 1203. The circumferential shift 1228 is provided in the displayed embodiment so that the electrode conductor wire electrically coupled to each segmented tip electrode is offset from a thermocouple that can also be present under each segmented tip electrode. In the present embodiment the second segmented tip electrode 1220 is shown with bordering strips of longitudinally extending substrate along the length of and on each side of the second segmented tip electrode 1220. Each strip of substrate is shown to include three irrigation flow holes 1207 that are generally evenly spaced along a working section 1226 of the tip electrode 1203. The second segmented tip electrode 1220 continues proximally over the shoulder 1227 of the tip electrode 1203 then deviates circumferentially around the tip electrode 1203 and continues proximally until terminating at an electrical conductor termination recess 1229. An electrode conductor wire 1230 is electrically coupled to the electrical conductor termination recess 1229 and a thermal sensor 1222 for the second segmented tip electrode 1220 is illustrated extending proximally from the tip electrode 1203.

Each of the segmented tip electrodes are bordered by a substrate that can be thermally and electrically nonconductive. The size of the segmented tip electrodes and the size of the substrate between the segmented tip electrodes can be varied depending on the desired effects and the application of the tip electrode 1203. In the illustrated embodiment each strip of substrate between the segmented tip electrodes includes three irrigation flow holes 1207 that have been spaced along a longitudinal axis of the tip electrode 1203. The current embodiment displays the irrigation flow holes 1207 as equally spaced, however, other quantities and spacing of the irrigation flow holes 1207 are contemplated. The irrigation flow holes 1207 can be fluidly coupled to an irrigation source and operate to distribute irrigation fluid to the exterior of the tip electrode 1203.

Figure 13:
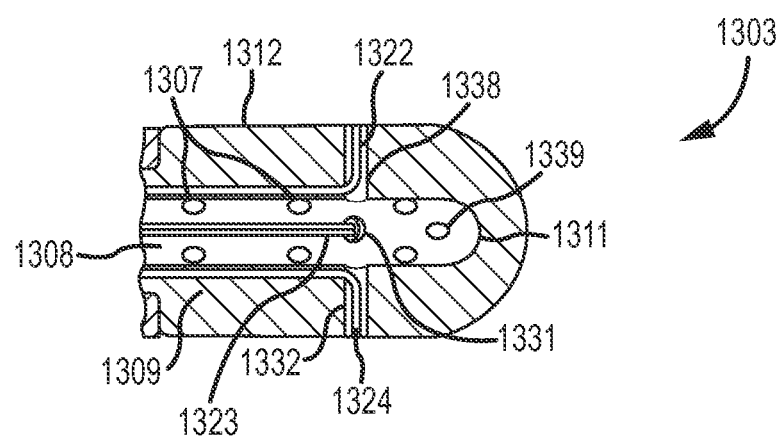
FIG. 13 depicts a cross-sectional view of a segmented tip ablation electrode assembly.

FIG. 13 illustrates a cross-sectional view of a tip electrode 1303 according to an embodiment of the disclosure. A cross-section of the tip electrode 1303 shows an electrically-insulative substrate 1309 comprising an outer surface 1312, an inner surface 1311, a first through channel 1338, a second through channel 1331, a third through channel 1332, and a plurality of irrigation flow holes 1307. The inner surface 1311 defines a receiving lumen 1308 and includes a fluid lumen alignment feature 1339. The electrically-insulative substrate 1309 is sized such that a first thermal sensor 1322, a second thermal sensor 1323, and a third thermal sensor 1324 can be placed within the receiving lumen 1308 and extend through the provided through channels. A distal end of each thermal sensor can terminate adjacent the outer surface 1312 of the electrically-insulative substrate 1309. A material can be used to bind or glue the distal end of each thermal sensor in place within its respective through channel. In some embodiments the material can be thermally conductive to improve the speed of the thermal sensor sensing any temperature changes occurring adjacent the thermal sensor at the outer surface 1312 of the electrically-insulative substrate 1309. In other embodiments the inner surface 1311 of the electrically-insulative substrate 1309 includes a fluid lumen alignment feature 1339. The fluid lumen alignment feature 1339 can be a protrusion, an indentation, a notch, or the like and can assist with properly positioning an irrigation lumen within the receiving lumen 1308.

Figure 14:
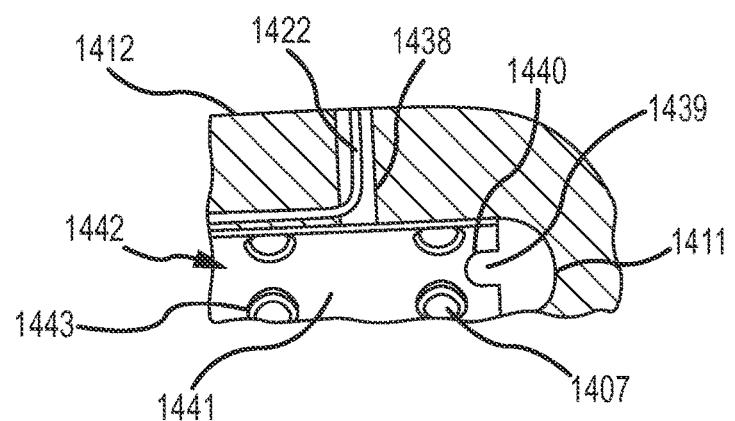
FIG. 14 depicts a cross-sectional view of an embodiment of an ablation electrode.

FIG. 14 illustrates a close up of the tip electrode 1403 of FIG. 13 with an irrigation sleeve 1441 positioned within the receiving lumen 1408. The irrigation sleeve 1441 comprises a plurality of outlets 1443 that are configured to align with irrigation flow holes 1407 within the electrically-insulative substrate 1409. The irrigation sleeve 1441 is aligned with the electrically-insulative substrate 1409 through the use of a registration relief 1440 on the irrigation sleeve 1441 and a fluid lumen alignment feature 1439 on the inner surface 1411 of the electrically-insulative substrate 1409. In an embodiment the irrigation sleeve 1441 can be glued to the receiving lumen 1408 of the electrically-insulative substrate 1409. The thermal sensor 1422 is provided with some thermal insulation from an irrigation fluid flowing through the tip electrode 1403 by the irrigation sleeve 1441. The thermal separation can allow the thermal sensor 1422 within the through channel 1438 to sense a more accurate reading of the temperature present at the outer surface 1412 of the electrically-insulative substrate 1409.

Figure 15:
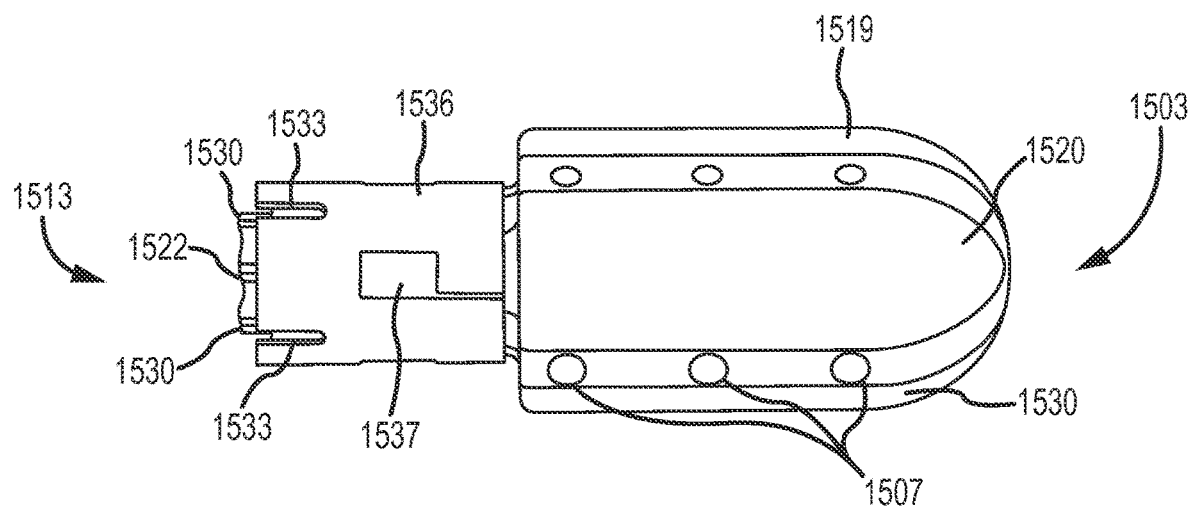
FIG. 15 is a diagrammatic view of a segmented electrode in accordance with an embodiment of the disclosure.
Figure 16:
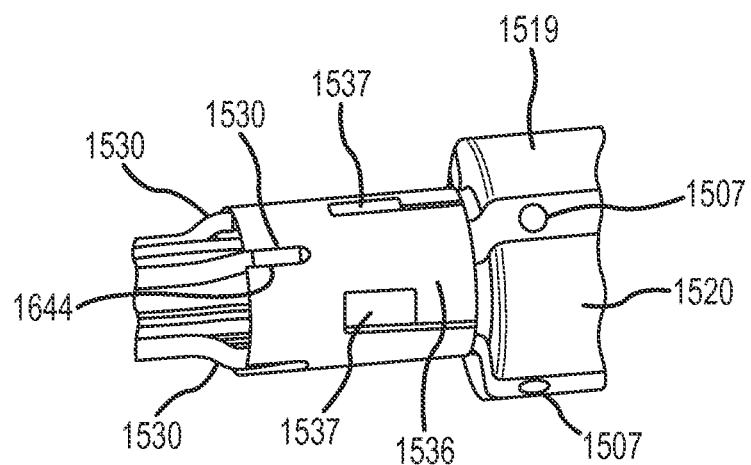
FIG. 16 is a fragmentary, isometric view of the segmented electrode of FIG. 15.

FIGS. 15 & 16 illustrate the tip electrode 1503 of FIG. 12 with an added insulation sleeve 1536. The insulation sleeve 1536 is placed over the proximal end 1513 of the tip electrode 1503 and coupled thereto. The insulation sleeve 1536 insulates the proximal end 1513 of the segmented tip electrodes from other components of the tip electrode 1503 and from the catheter shaft that the tip electrode 1503 is coupled to. The insulation sleeve 1536 comprises a relief window 1537 and at least one recess gap 1533. The relief window 1537 is configured for engagement with other components of a catheter body, and the at least one recess gap 1533 can allow for the electrode conductor wire 1530 and the electrical conductor termination recess 1529 to more easily couple to each other.

Figure 17:
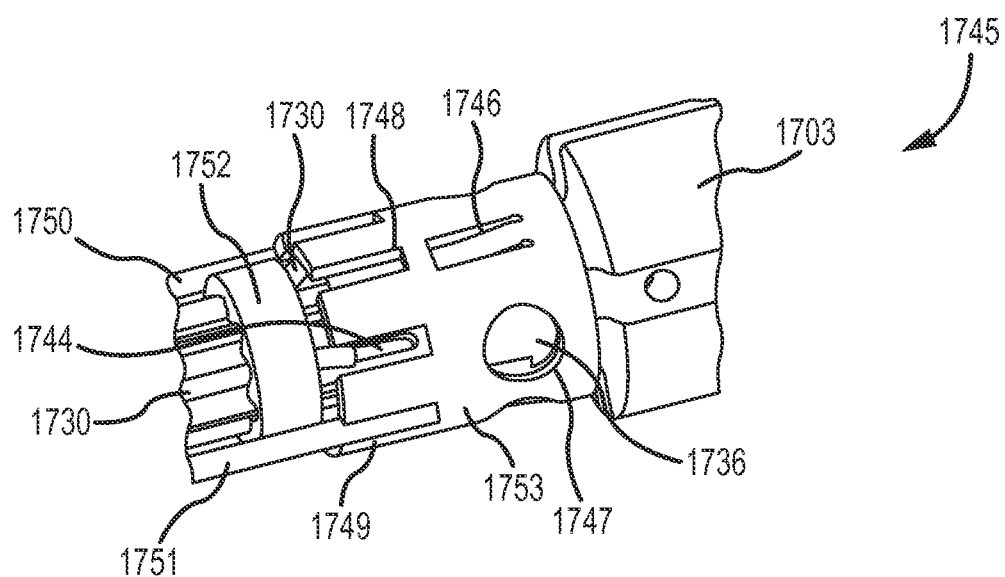
FIG. 17 depicts a fragmentary, isometric view of a portion of a segmented tip assembly in accordance with an embodiment of the disclosure.

FIG. 17 displays the tip electrode of FIGS. 15 & 16 now formed into a tip assembly 1745 with a deflection pull ring 1753 and a conductor grooming component 1752 added thereto. The deflection pull ring 1753 is configured to lock on to the insulation sleeve 1736. The deflection pull ring 1753 can comprise at least one clip lock 1746, at least one pullwire recess 1749, and optionally, an anchor hole 1747. The at least one clip lock 1746 can be configured to couple with a corresponding relief opening in the insulation sleeve 1736. The clip lock 1746 can be configured such that movement of the deflection pull ring 1753 over the insulation sleeve 1736 can cause the clip lock 1746 to settle within a relief opening and lock the deflection pull ring 1753 to a proximal end of the tip electrode 1703. The at least one pullwire recess 1749 is configured to receive a distal end of a pullwire 1751. In the illustrated embodiment, a first pullwire recess (not shown) is coupled to a first pullwire 1750. A second pullwire 1751 is also coupled to a second recess 1749. In the current embodiment the first and second pullwire recesses are set across the catheter from each other. In other embodiments, the deflection pull ring 1753 can comprise one or multiple pullwire recesses that are configured to couple to pullwires within a catheter body. The optional anchor hole 1747 is one of several surface modification possibilities that can be used to promote adhesion between the deflection pull ring 1753 and a catheter body that can be coupled thereto. The deflection pull ring 1753 can also be configured such that deflection gaps on the proximal end can match with the recess gap 1744 of the insulation sleeve 1736. These deflection gaps allow for electrical conductor wires 1730 to couple to the tip electrode 1703. The conductor grooming component 1752 can be used to position the various lumens and wires such that proper spacing is kept throughout the length of the catheter. In another embodiment an insulation sleeve 1736 can comprise a positive feature that can clip or lock into a negative feature of a deflection pull ring 1753. A more detailed discussion illustration is provided in FIG. 20.

Figure 18:
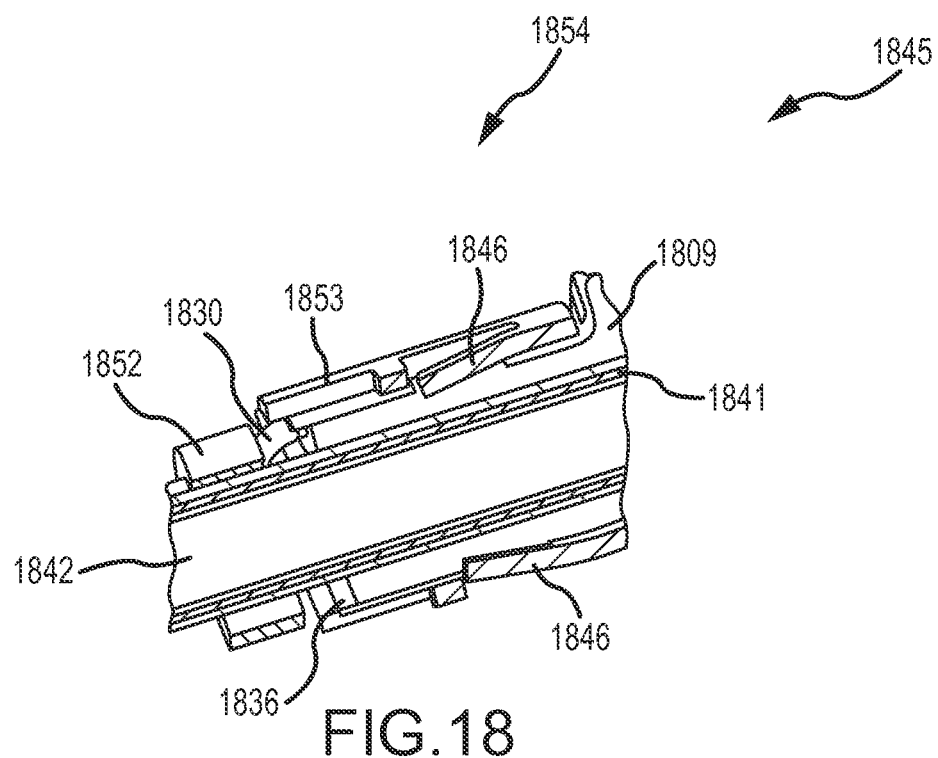
FIG. 18 is a cross-sectional view of a proximal portion of a tip electrode in accordance with an embodiment of the disclosure.

FIG. 18 illustrates a cross-sectional view of a tip assembly 1845. The tip assembly 1845 comprises an electrically-insulative substrate 1809 forming a receiving lumen for receiving an irrigation sleeve 1841 The irrigation sleeve 1841 forms an irrigation lumen 1842. An electrode conductor wire 1830 is coupled to a thin layer of conductive material that has been deposited on the electrically-insulative substrate 1809. An insulation sleeve 1836 is placed over a proximal portion 1854 of the electrically-insulative substrate 1809. A deflection pull ring 1853 is then placed over the insulation sleeve 1836 and coupled thereto through at least one clip lock 1846. Located proximally of the tip assembly 1845 the electrode conductor wire 1830 passes through a conductor grooming component 1852.

Figure 19:
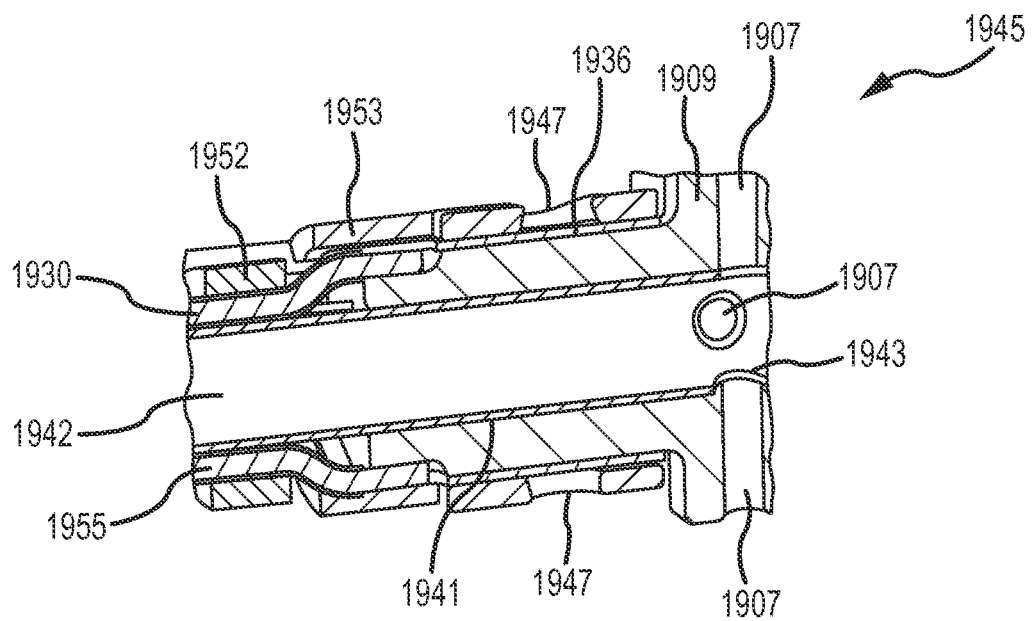
FIG. 19 depicts a cross-sectional view of a proximal portion of a tip electrode.

FIG. 19 illustrates a cross-sectional view of another embodiment of a tip assembly 1945. The tip assembly comprises an electrically-insulative substrate 1909 forming a void configured to receive an irrigation sleeve 1941, and a plurality of irrigation flow holes 1907. The irrigation lumen comprises an irrigation lumen 1942 and a plurality of outlets 1943 that are configured to fluidly couple with the irrigation flow holes 1907 present in the electrically-insulative substrate 1909. A first electrode conductor wire 1930 and a second electrode conductor wire 1955 are coupled to separate thin layers of conductive material that has been deposited on the electrically-insulative substrate 1909. An insulation sleeve 1936 is configured to be placed around a proximal portion 1954 of the electrically-insulative substrate 1909. A deflection pull ring 1953 can then be positioned around the insulation sleeve 1936 and coupled thereto. The deflection pull ring 1953 can further comprise at least one anchor hole 1947 that can aid in promoting adhesion between the deflection pull ring 1953 and a catheter body or other component. A conductor grooming component 1952 can be located proximally of the tip assembly 1945 to provide proper alignment for the irrigation sleeve, the first and second electrode conductor wires 1930, 1955 and any other components passing therethrough.

Figure 20:
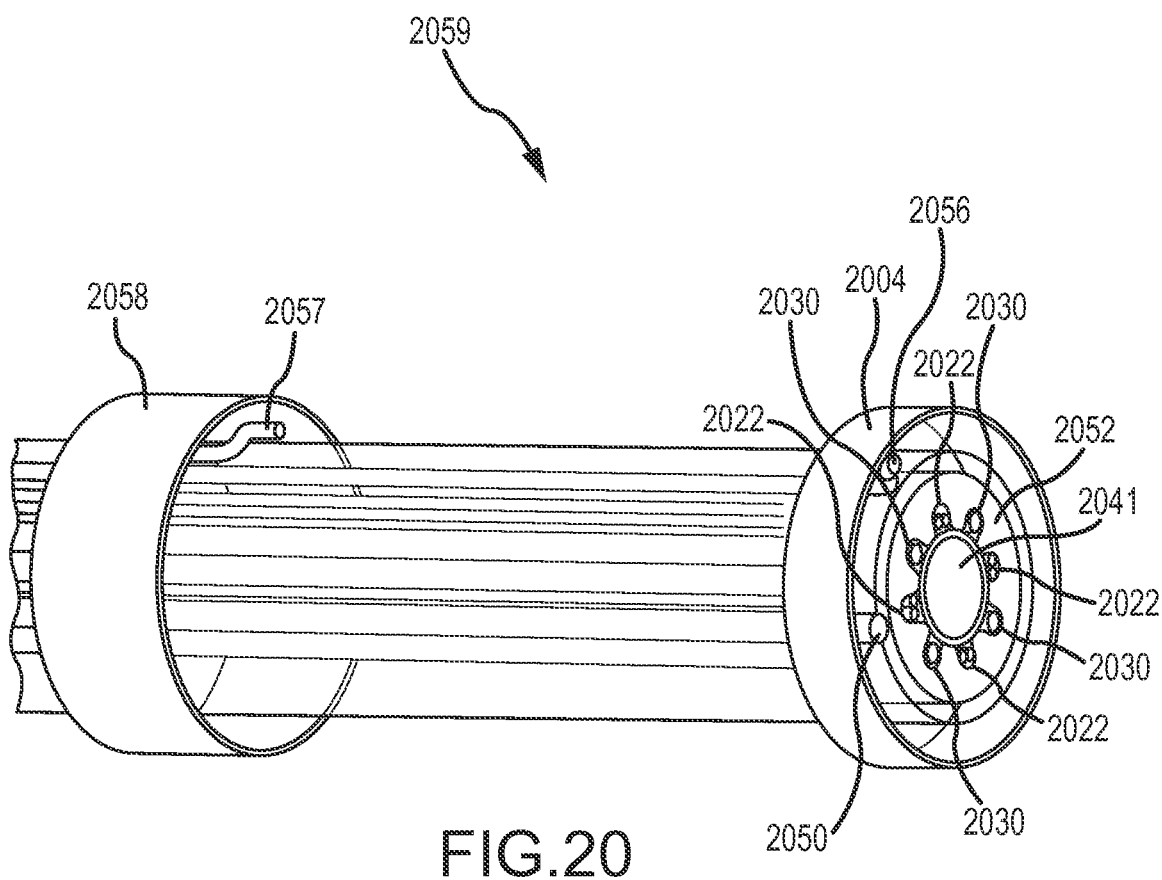
FIG. 20 depicts an isometric partially transparent view of a catheter body in accordance with an embodiment of the disclosure.

FIG. 20 displays a portion of a catheter body 2059. The catheter body comprises a first ring electrode 2004, a second ring electrode 2058, and a conductor grooming component 2052. The first ring electrode 2004 is coupled to a first ring electrode conducting wire 2056 and the second ring electrode 2058 is connected to a second electrode conducting wire 2057. The conductor grooming component 2052 is configured such that it comprises at least one cavity extending therethrough. The cavity is designed to facilitate the proper placement and constriction of elements passing through the catheter body 2059. In the illustrated embodiment the cavity comprises a large center portion that allows an irrigation sleeve 2041 to pass. The conductor grooming component 2052 further comprises a number of smaller lumens connected to the main cavity that are configured to contain and/or direct the placement of passing electrode conductor wires 2030, thermal sensors 2022, and other catheter components. In some embodiments, a plurality of conductor grooming components 2052 are included throughout the catheter body 2059 to control the movement of various catheter components. This can be especially important when a catheter is used during a procedure, twisted through a patient's anatomy, and deflected by a physician or other user.

Figure 23:
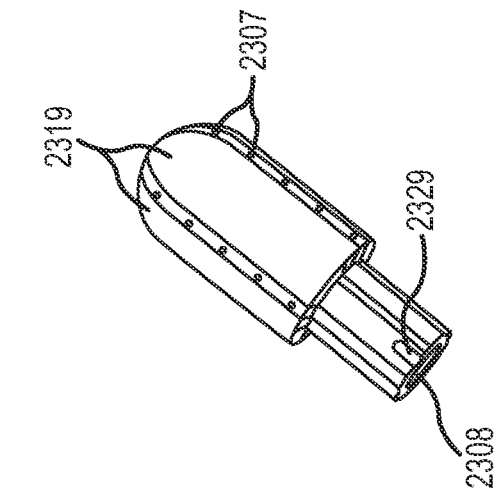
FIGS. 21-23 depict several stages in a manufacturing process for a tip electrode.
Figure 22:
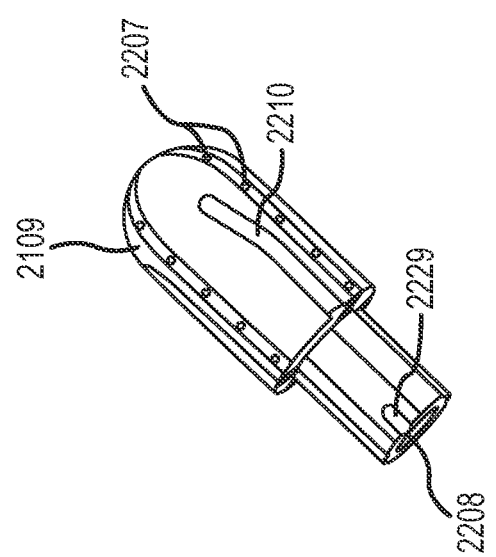
Figure 21:
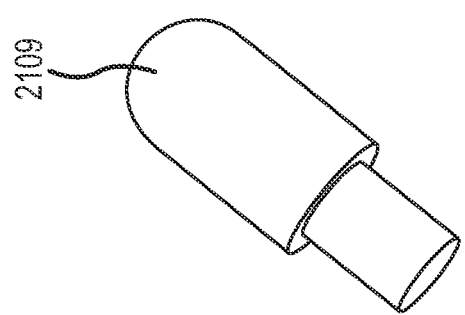

FIGS. 21-23 show a method of manufacturing a tip electrode comprising segmented tip electrodes according to an embodiment of the disclosure. FIG. 21 shows an electrically-insulative substrate 2109 that has been formed in to a desired tip electrode shape. Other configurations and shapes are contemplated within this disclosure, the illustrated embodiment is just one of the possible shapes. As seen in FIG. 22 the electrically-insulative substrate 2109 can then be machined such that desired features can be added to the tip electrode. In the illustrated embodiment at least one conductor recess 2229, at least one thermal sensor channel 2210, a receiving lumen 2208, and a plurality of irrigation flow holes 1907 have been added to the electrically-insulative substrate 2109. FIG. 23 illustrates the tip electrode 2303 including at least one segmented tip electrode 2319. The at least one segmented tip electrode 2319 can be formed by depositing thin layers of conductive materials on to the electrically-insulative substrate. The thin layers can be deposited by various means including: low temperature print manufacturing (with or without sintering), electroplating, sputter deposition, and pulsed laser deposition or combinations of the above.

Figure 24:
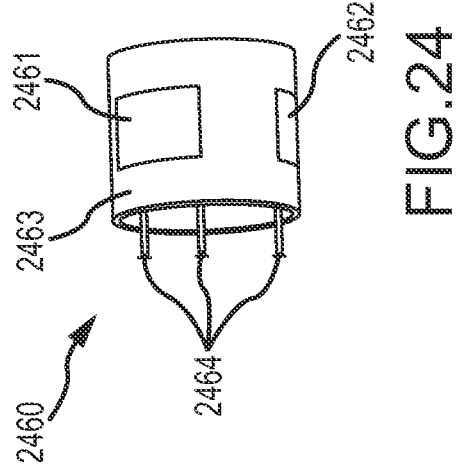
FIG. 24 is an isometric view of a segmented electrode subassembly.

FIG. 24 illustrates a segmented electrode subassembly 2460. This embodiment comprises a first electrode segment 2461, a second electrode segment 2462, and a third electrode segment (not shown). It further comprises a polymeric skin 2463 and separate conductor wires 2464 coupled to each of the electrode segments. A fully assembled segmented electrode subassembly 2460 can be coupled to a catheter body and utilized as a segmented electrode. A single segmented electrode subassembly 2460 can be used within a catheter or, in other embodiments, multiple segmented electrode subassemblies 2460 can be added to a catheter at varying desired locations. By using the segmented electrode subassembly 2460 as described herein the location and tolerances of the electrodes can be better controlled across all catheters using a specific segmented electrode assembly 2460 and this can be taken into account for electrophysiological mapping or location sensing. In one embodiment, the segmented electrode assembly 2640, as well as the segmented tip electrode disclosed herein, can be selectively energized such that specific segmented electrodes can deliver RF energy to a target tissue. In a further embodiment, RF power can be selectively delivered from segmented electrodes that are in contact with a tissue. In a yet further embodiment, the segmented electrodes can derive orientation-independent, bipolar signals, activation direction, and/or conduction velocity. This is described in co-pending U.S. provisional application No. 61/855,058, which is hereby incorporated by reference as though fully set forth herein.

Figure 25:
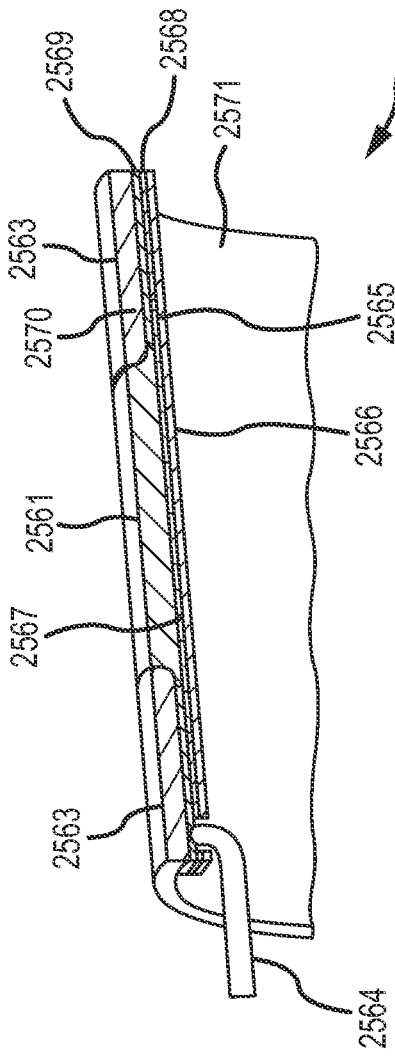
FIG. 25 depicts a fragmentary, cross-sectional view of a portion of a segmented electrode subassembly.

FIG. 25 displays a cross-sectional view of one embodiment of a segmented electrode subassembly 2560. The segmented electrode subassembly comprises an inner electrode support substrate 2565, a layer of conductive material 2516, an outer support segment 2569, an electrode segment 2561, and a polymeric skin 2563. The innermost layer of the segmented electrode subassembly 2560 can be the inner electrode support substrate 2565. An inner surface 2566 of this layer defines a subassembly lumen 2571. A thin layer of conductive material 2516 is then deposited on an inner support outer surface 2567. An electrode segment 2561 is electrically coupled to the layer of conductive material 2516 and the outer support segment 2569 is placed overtop the electrode segment 2561 to secure the component to the segmented electrode subassembly 2560. A polymeric skin 2563 is the final outer layer of the segmented electrode subassembly and is adjacent an outer support outer surface 2570. The polymeric skin 2563 can comprise the same material as a catheter body to which the segmented electrode subassembly 2560 will be added. A segmented electrode conductor wire 2564 can be electrically coupled to the conductive material 2516 and can be used to transmit electrical signals received by the electrode segment 2561.

Figure 26:
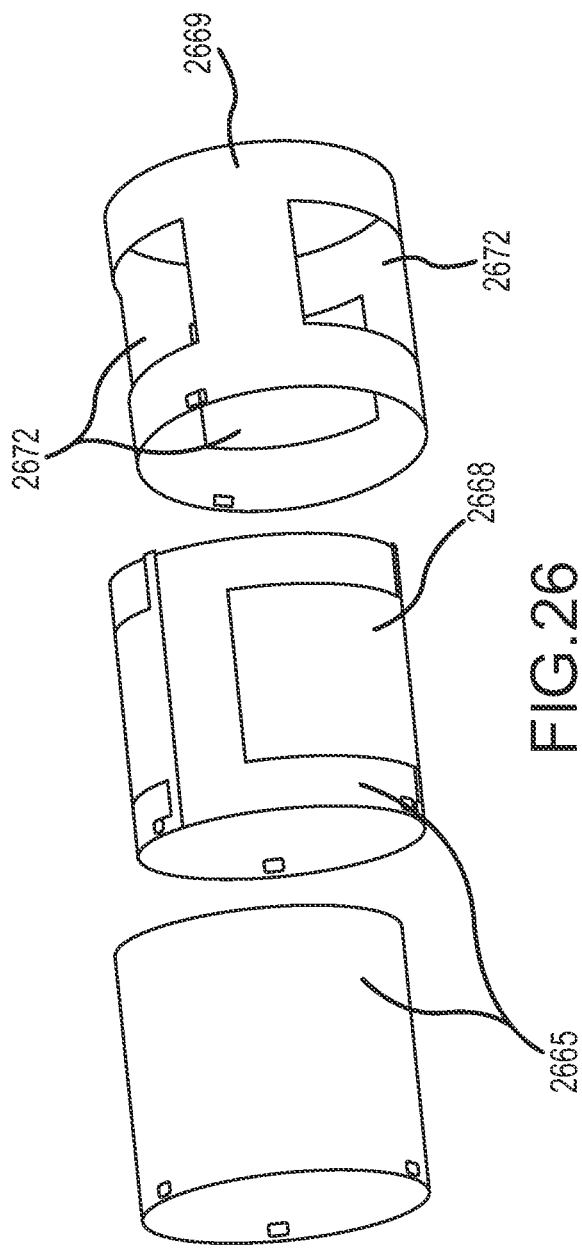
FIG. 26 depicts isometric views of various components of an embodiment of a segmented electrode subassembly.

FIG. 26 separately shows several of the components of an embodiment of a segmented electrode subassembly. The inner electrode support substrate 2665 is shown both before any other materials have been added and after the conductive material 2668 has been disposed thereon. The outer support segment 2669 is also shown isometrically before it has been placed over the conductive layer 2668 and used to secure an electrode segment to the subassembly. A plurality of notches 2672 are shown that will help secure electrode segments to the segmented electrode subassembly.

FIG. 27 separately shows several of the components of an embodiment of a segmented electrode subassembly separately and in various stages of manufacture. The outer support segment 2769 and the polymeric skin 2763 are shown joined together and with matching notches 2772 cut in both. These notches 2772 are spaced and sized to secure the electrode segment components 2773, 2774, 2775 to the segmented electrode subassembly. These electrode segment components 2773, 2774, 2775 can comprise an electrode face 2776, an electrode ridge 2777, and an electrode back 2778. The electrode face 2776 can be used to sense electrical activity to the exterior of the segmented electrode subassembly or can be used for positioning information with an electroanatomical mapping system. The electrode back 2778 can be electrically coupled to a conductive material layer 2616 or other material that can transmit the electrical signals received by the electrode segment components 2773, 2774, 2775. The outer support segment 2769 and the polymeric skin 2763 can be positioned so that a portion of each is contacting the electrode ridge 2777 and can be used to help secure an electrode segment component to the segmented electrode subassembly. The embodiment also shows the three electrode segment components placed within the notches 2772 provided within the outer support segment 2769 and the polymeric skin 2763.

FIG. 28 shows an exemplary process through which mass production of a segmented electrode subassembly can occur. A plurality of inner subassemblies 2881 are produced by depositing conductive material 2880 in a predetermined pattern on a length of inner support segment 2879. The inner subassemblies 2881 can then be cut to the desired length and electrode segment components can be coupled thereto. Similarly, a plurality of outer subassemblies 2883 are produced by matching the notches 2872 of a length of outer support member 2882 and a length of polymeric skin 2863. The outer subassemblies 2883 can then be cut to the desired length and joined with the cut inner subassemblies 2881. Alternatively the inner subassemblies 2881 can have electrode segment components coupled thereto before being cut to length, the outer subassemblies 2883 can be joined with the inner subassemblies 2881 and various lengths of segmented electrode subassemblies can be cut or made therefrom.

Figure 29D:
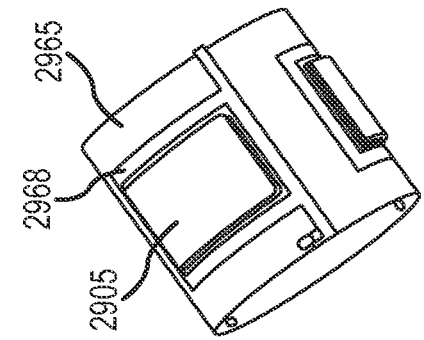
FIGS. 29A to 29D depict isometric views of components of a segmented electrode subassembly.
Figure 29C:
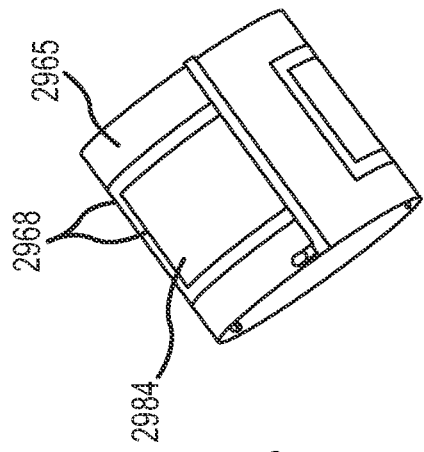
Figure 29B:
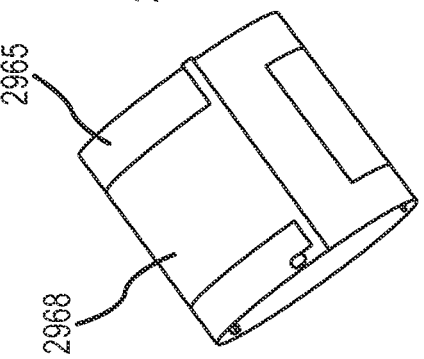
Figure 29A:
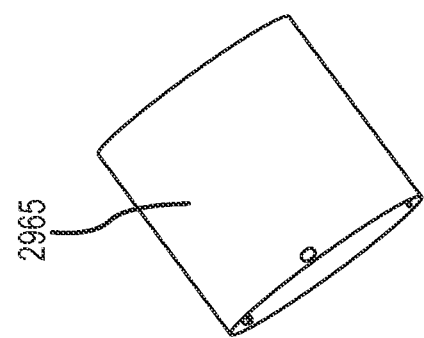

FIGS. 29A to 29D illustrate another embodiment of several of the components of a segmented electrode subassembly. The inner electrode support substrate 2965 is shown both before any other materials have been added and after the conductive material 2968 has been disposed thereon. FIG. 29C illustrates a second layer of conductive material 2984 coupled to the initial layer of conductive material 2968. A segmented electrode 2905 can then be electrically coupled to the first and second layers of conductive substrate 2968, 2984. The segmented electrode 2905 can comprise a cold soldered component or a material plated onto the layers of conductive substrate 2968, 2984. In a further embodiment the segmented electrode 2905 can be manufactured using a MICA Freeform process.

Figure 31:
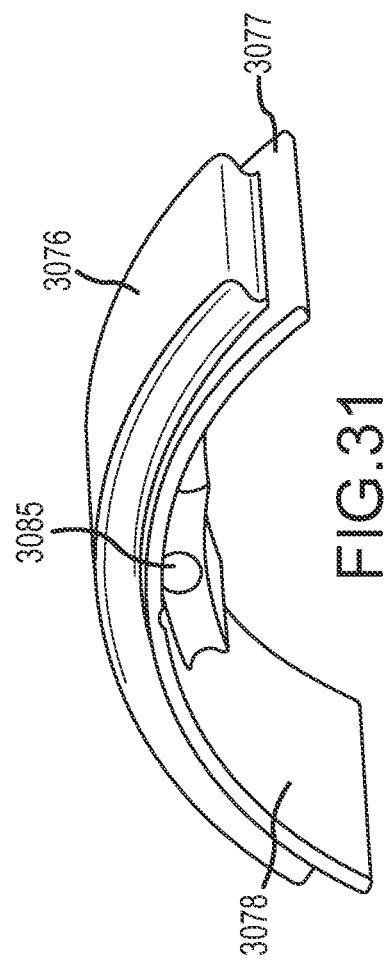
FIG. 31 depicts an isometric view of the segmented electrode of FIG. 30.
Figure 30:
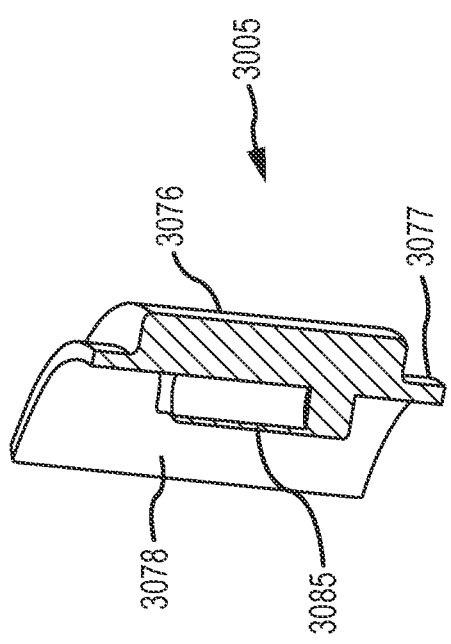
FIG. 30 depicts an isometric cross-sectional view of an embodiment of a segmented electrode.

FIGS. 30 and 31 depict a cross-section and an isometric view of an embodiment of a segmented electrode 3005, respectively. The segmented electrode 3005 comprises an electrode face 3076, an electrode ridge 3077, and an electrode back 3078. In some embodiments, the electrode back 3078 is configured to be electrically coupled directly to a conductive substrate disposed on a catheter shaft. In other embodiments the segmented electrode 3005 is configured such that an electrode wire (not shown) can be coupled to the segmented electrode 3005. In the current embodiment an electrode wire can be coupled to a recess 3085 disposed on the back of the segmented electrode 3005.

Figure 32:
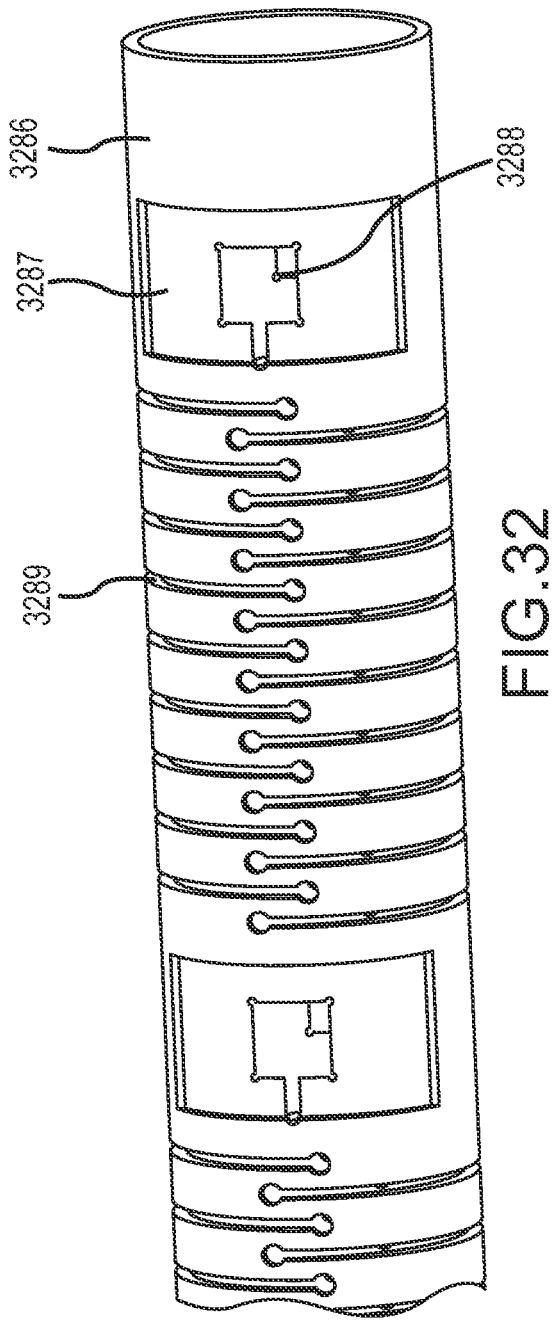
FIG. 32 depicts an isometric view of an embodiment of a flexible catheter support.

FIG. 32 illustrates an embodiment of a polyimide tube that can be used with an embodiment of the disclosure. The polyimide tube 3286 can be laser machined such that it comprises an electrode indent 3287, a recess notch 3288, and a plurality of linear gaps 3289. The electrode indent 3287 can be sized and configured such that a segmented electrode can be set within the indent. In the current embodiment the recess notch 3288 can be sized and configured such that the back of a segmented electrode like that seen in FIGS. 30 and 31 can be placed through the recess notch 3288. This can allow for electrode wires to be connected to the back of the segmented electrode and also be within a lumen of the polyimide tube 3286. The polyimide tube can further comprise a plurality of linear gaps 3289 which can be configured to increase flexibility of the polyimide tube 3286 or to improve planarity, curve type, or other characteristics of the polyimide tube 3286 and any catheter that the polyimide tube 3286 is placed within.

Figure 33:
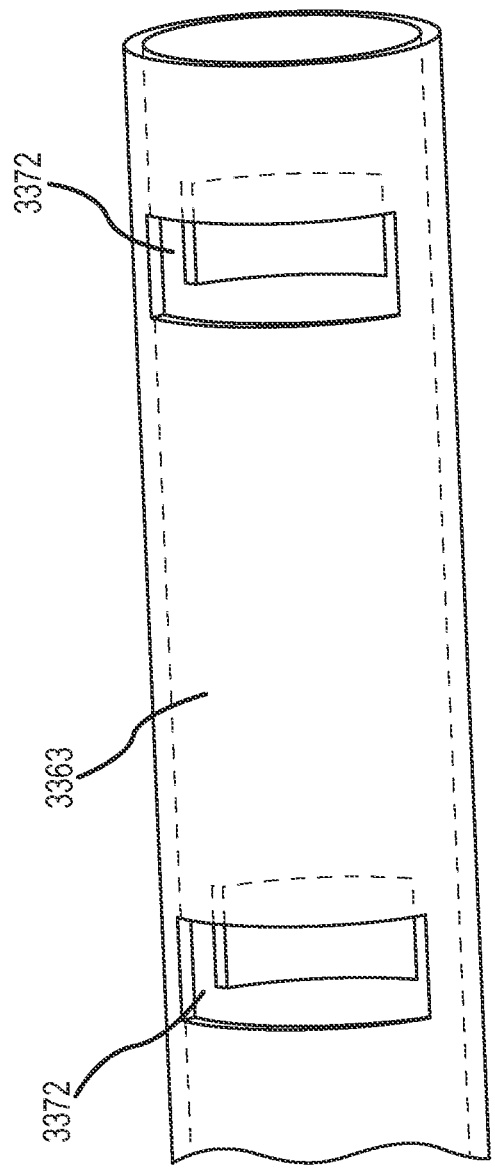
FIG. 33 depicts an isometric view of an embodiment of a catheter skin.

FIG. 33 illustrates a polymeric skin 3363 that can be placed over a polyimide tube. In the illustrated embodiment the polymeric skin 3363 comprises a plurality of notches 3372 that can be sized and configured to be placed over a plurality of segmented electrodes. The segmented electrodes can be coupled to a polyimide tube such as that illustrated in FIG. 32.

Figure 34:
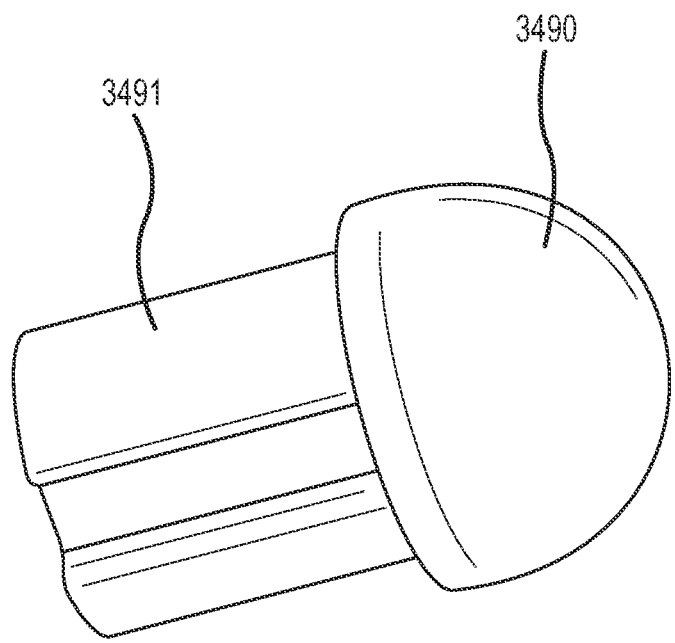
FIG. 34 depicts an isometric view of an embodiment of a tip electrode.

FIG. 34 illustrates a tip electrode 3490 that can be used within a catheter. The tip electrode 3490 comprises a proximal electrode portion 3491 that can be configured to be placed within a catheter body.

Figure 35:
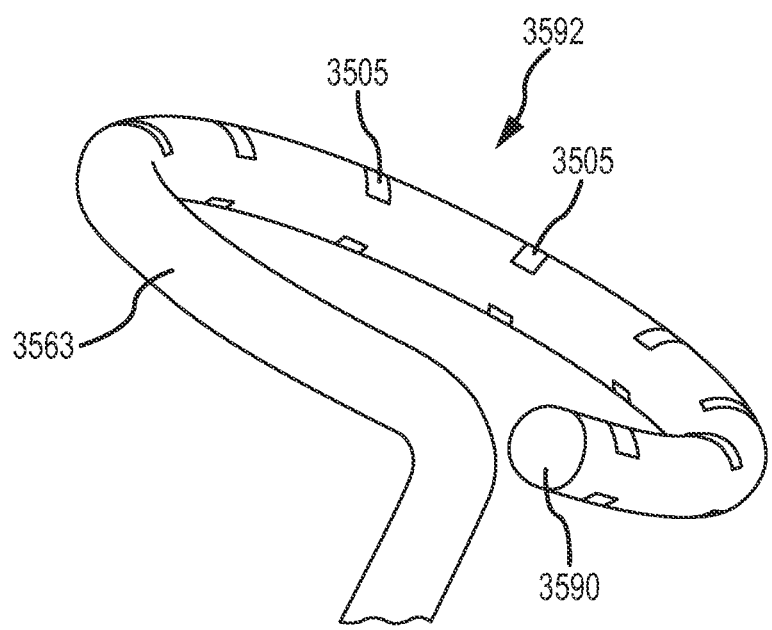
FIG. 35 depicts an isometric view of a circular catheter.

FIG. 35 illustrates a circular catheter 3592. The circular catheter can comprise a plurality of segmented electrodes 3505, a tip electrode 3590, and a polymeric skin 3563. In one embodiment the circular catheter 3592 can comprise the various components illustrated in FIGS. 30 through 34. The plurality of segmented electrodes 3505 can be arranged such that pairs of the electrodes can be offset at 180° around a circumference of the polymeric skin 3563.

The pairs of segmented electrodes can be spaced from each other at varying distances. In some embodiments the pairs of segmented electrodes can be evenly spaced. In other embodiments the pairs of segmented electrodes can be spaced at varying distances along the length of the catheter depending on the use of the catheter. In yet other embodiments the placement of the electrodes can also be varied. These embodiments can include one, two, three, or four segmented electrodes spaced around a circumference of the catheter.

What is claimed is:

1. A tip electrode comprising:
an electrically-insulative substrate comprising a receiving lumen, a plurality of irrigation flow holes, a tip portion, a proximal portion, and at least two thermal sensor channels defined in a laterally facing exterior surface of the tip portion of the electrically-insulative substrate;
at least two segmented tip electrodes deposited on the outer surface of the tip portion, each of the segmented tip electrodes disposed over a respective one of the thermal sensor channels, thereby covering each respective one of the thermal sensor channels, wherein the at least two segmented tip electrodes are thermally isolated from one another, such that a thermal sensor disposed in each of the at least two thermal sensor channels is configured to obtain an independent temperature reading of a respective segmented tip electrode, the segmented tip electrodes extending from a most proximal edge of the tip portion to a distal end of the tip portion;
an insulation sleeve configured to circumferentially surround and electrically insulate the proximal portion of the segmented tip electrodes, the insulation sleeve comprising at least one recess gap;
a deflection pull ring configured to mate with the insulation sleeve; and
a conductor grooming component proximal to the electrically-insulative substrate and configured to secure a plurality of conductor wires;
wherein a portion of an inner surface of the electrically-insulative substrate defines the receiving lumen and the irrigation flow holes extend radially through the electrically-insulative substrate and terminate adjacent an outer surface of the electrically-insulative substrate, wherein the electrically-insulative substrate electrically insulates the at least two segmented tip electrodes from one another, and
wherein the receiving lumen is fluidly coupled to the plurality of irrigation flow holes and the receiving lumen is configured to be fluidly coupled to a catheter body.

2. The tip electrode according to claim 1, wherein the thermal sensor channels extend from a most proximal edge of the tip portion of the electrically-insulative substrate, distally along the outer surface of the tip portion of the electrically-insulative substrate.

3. The tip electrode according to claim 1 further comprising a fluid lumen alignment feature coupled to the inner surface of the electrically-insulative substrate and configured for coupling with the irrigation sleeve.

4. The tip electrode according to claim 1 further comprising an electrical conductor termination recess configured for coupling to a conductor wire.

5. The tip electrode according to claim 1 further comprising a through channel extending from the inner surface to the outer surface of the electrically-insulative substrate.

6. The tip electrode according to claim 5 further comprising a thermal sensor disposed within the through channel.

7. The tip electrode according to claim 1, wherein the deflection pull ring comprises at least one clip lock configured to mate with a relief opening of the insulation sleeve.

8. The tip electrode of claim 1, wherein the at least two thermal sensor channels terminate proximally with respect to a distal end of the electrically-insulative substrate.

9. The tip electrode of claim 1, wherein:
the at least two thermal sensor channels are distributed around an outer circumference of the electrically-insulative substrate; and
the plurality of irrigation flow holes are distributed between each of the at least two thermal sensor channels.

10. The tip electrode of claim 1, wherein the at least two thermal sensor channels define openings that are open to the outer surface of the tip portion along an entirety of their length, wherein the segmented tip electrodes cover the openings of the at least two thermal sensor channels along the entirety of their length.

11. The tip electrode of claim 1, wherein the conductor grooming component defines a central lumen through which the irrigation sleeve passes and a plurality of lumens connected to the central lumen through which the plurality of conductor wires pass.

* * * * *